US012544051B2

(12) United States Patent
Harden et al.

(10) Patent No.: US 12,544,051 B2
(45) Date of Patent: Feb. 10, 2026

(54) DEVICES, SYSTEMS AND METHODS FOR TREATING THE SKIN

(71) Applicant: HydraFacial LLC, Long Beach, CA (US)

(72) Inventors: Daniel Harden, Carmel, CA (US); Elliot Ortiz, Pinole, CA (US); Yale Shaw, San Francisco, CA (US); Daniel Cheung, San Francisco, CA (US); Katie Rozporka, San Jose, CA (US); Stacie Depner, Anaheim, CA (US); Sounak Maisuri, Fullerton, CA (US)

(73) Assignee: HydraFacial LLC, Long Beach, CA (US)

( * ) Notice: Subject to any disclaimer, the term of this patent is extended or adjusted under 35 U.S.C. 154(b) by 156 days.

(21) Appl. No.: 18/690,694

(22) PCT Filed: Sep. 9, 2022

(86) PCT No.: PCT/US2022/076203

§ 371 (c)(1),
(2) Date: Mar. 8, 2024

(87) PCT Pub. No.: WO2023/039524

PCT Pub. Date: Mar. 16, 2023

(65) Prior Publication Data

US 2024/0389986 A1 Nov. 28, 2024

Related U.S. Application Data

(60) Provisional application No. 63/243,053, filed on Sep. 10, 2021.

(51) Int. Cl.
*A61B 17/00* (2006.01)

(52) U.S. Cl.
CPC .... *A61B 17/00* (2013.01); *A61B 2017/00734* (2013.01); *A61B 2017/00761* (2013.01); *A61B 2217/005* (2013.01); *A61B 2217/007* (2013.01)

(58) Field of Classification Search
CPC .......... A61B 17/00; A61B 2017/00734; A61B 2017/00761; A61B 2217/005; A61B 2217/007
See application file for complete search history.

(56) References Cited

U.S. PATENT DOCUMENTS

| | | |
|---|---|---|
| 1,651,585 A | 12/1927 | Clair |
| D117,295 S | 10/1939 | Smith |

(Continued)

FOREIGN PATENT DOCUMENTS

| | | |
|---|---|---|
| AT | 400305 | 12/1995 |
| AU | 1014299 | 5/1999 |

(Continued)

OTHER PUBLICATIONS

Amazon, Fazjeune 7 Color LED Light, LED Face Mask Skin Rejevenation PDT Photon Facial Skin Care Mask Skin Tightening Lamp SPA Face Device Beauty Salon Equipment Anti-aging RemoveWrinkle, Customer reviewed on Sep. 2020, retrieved from internet at https://www.amazon.com/FAZJEUNE- Rejuvenation-Tightening-Equipment-Anti-aging/dp/B08B4M8RQQ/ref=psdc_11061121_t3_B08ZSPZSF4.

(Continued)

*Primary Examiner* — Ashley L Fishback
(74) *Attorney, Agent, or Firm* — Knobbe, Martens, Olson & Bear, LLP

(57) ABSTRACT

According to some embodiments, a skin treatment system comprises a main body portion, a waste container configured to be removably secured to the main body portion, a tip configured to be removably secured to the main body (Continued)

portion, a pump, at least one fluid delivery conduit placing an interior of a treatment material container secured to the receiving area in fluid communication with the tip, and at least one waste conduit placing the at least one waste port of the tip in fluid communication with the pump.

20 Claims, 15 Drawing Sheets

(56) References Cited

U.S. PATENT DOCUMENTS

D151,807 S 11/1948 Berkowitz
2,608,032 A 8/1952 Garver
2,631,583 A 3/1953 Lavergne
2,701,559 A 2/1955 Cooper
2,712,823 A 7/1955 Kurtin
2,867,214 A 1/1959 Wilson
2,881,763 A 4/1959 Robbins
2,921,585 A 1/1960 Schumann
3,037,509 A 6/1962 Schutz
3,085,573 A 4/1963 Meyer et al.
3,214,869 A 11/1965 Stryker
3,468,079 A 9/1969 Kaufman
3,476,112 A 11/1969 Elstein
3,481,677 A 12/1969 Abrahamson
3,505,993 A 4/1970 Lewes et al.
3,560,100 A 2/1971 Spatz
3,574,239 A 4/1971 Sollerud
3,608,553 A 9/1971 Balamuth
3,715,838 A 2/1973 Young et al.
3,865,352 A 2/1975 Nelson et al.
3,866,264 A 2/1975 Engquist
D237,776 S 11/1975 Arassa et al.
D237,863 S 12/1975 Peters et al.
3,930,598 A 1/1976 Slagle
3,948,265 A 4/1976 Al Ani
3,964,212 A 6/1976 Karden
3,968,789 A 7/1976 Simoncini
3,977,084 A 8/1976 Sloan
4,121,388 A 10/1978 Wilson
4,155,721 A 5/1979 Fletcher
4,170,821 A 10/1979 Booth
4,182,329 A 1/1980 Smit et al.
4,203,431 A 5/1980 Abura et al.
D255,325 S 6/1980 Hoyt
4,216,233 A 8/1980 Stein
4,225,254 A 9/1980 Holberg et al.
D258,348 S 2/1981 Hoyt
D259,921 S 7/1981 Hartmann
D260,176 S 8/1981 Boschetti et al.
4,289,158 A 9/1981 Nehring
4,299,219 A 11/1981 Norris, Jr.
4,342,522 A 8/1982 Mackles
4,378,804 A 4/1983 Cortese
4,500,222 A 2/1985 Clading-Boel
4,560,373 A 12/1985 Sugino et al.
D288,293 S 2/1987 Arvans
4,646,480 A 3/1987 Williams
4,646,482 A 3/1987 Chitjian
4,655,743 A 4/1987 Hyde
4,671,412 A 6/1987 Gatten
4,676,749 A 6/1987 Mabille
D290,999 S 7/1987 Novak
4,706,676 A 11/1987 Peck
4,718,467 A 1/1988 Di Gianfilippo et al.
4,754,756 A 7/1988 Shelanski
4,757,814 A 7/1988 Wang et al.
4,764,362 A 8/1988 Barchas
4,795,421 A 1/1989 Blasius, Jr. et al.
4,811,734 A 3/1989 McGurk-Burleson et al.
4,836,192 A 6/1989 Abbate
4,866,202 A 9/1989 Weil
4,875,287 A 10/1989 Creasy et al.
4,886,078 A 12/1989 Shiffman
4,887,994 A 12/1989 Bedford
4,900,316 A 2/1990 Yamamoto
4,917,086 A 4/1990 Feltovich et al.
4,925,450 A 5/1990 Imonti et al.
D308,480 S 6/1990 Hoyt
4,940,350 A 7/1990 Kim
4,957,747 A 9/1990 Stiefel
4,990,841 A 2/1991 Elder
5,006,004 A 4/1991 Dirksing et al.
5,006,339 A 4/1991 Bargery et al.
5,012,797 A 5/1991 Clarke
D317,719 S 6/1991 Hestehave et al.
5,035,089 A 7/1991 Tillman et al.
5,037,431 A 8/1991 Summers et al.
5,037,432 A 8/1991 Molinari
5,054,339 A 10/1991 Yacowitz
5,100,412 A 3/1992 Rosso
5,100,424 A 3/1992 Jang
5,119,839 A 6/1992 Rudolph
5,122,153 A 6/1992 Harrel
5,171,215 A 12/1992 Flanagan
5,192,269 A 3/1993 Poli et al.
5,207,234 A 5/1993 Rosso
5,217,455 A 6/1993 Tan
5,222,956 A 6/1993 Waldron
5,242,433 A 9/1993 Smith et al.
5,254,109 A 10/1993 Smith et al.
5,290,273 A 3/1994 Tan
5,368,581 A 11/1994 Smith et al.
5,387,215 A 2/1995 Fisher
5,391,151 A 2/1995 Wilmot
5,417,674 A 5/1995 Smith et al.
5,419,772 A 5/1995 Teitz et al.
5,423,803 A 6/1995 Tankovich et al.
5,437,372 A 8/1995 Per-Lee
5,441,490 A 8/1995 Svedman
5,460,620 A 10/1995 Smith et al.
5,470,323 A 11/1995 Smith et al.
5,484,427 A 1/1996 Gibbons
5,490,736 A 2/1996 Haber et al.
5,512,044 A 4/1996 Duer
5,562,642 A 10/1996 Smith et al.
5,562,643 A 10/1996 Johnson
5,611,687 A 3/1997 Wagner
5,612,797 A 3/1997 Clarke
5,618,275 A 4/1997 Bock
5,626,631 A 5/1997 Eckhouse
5,658,323 A 8/1997 Miller
5,658,583 A 8/1997 Zhang et al.
5,674,235 A 10/1997 Parisi
5,676,643 A 10/1997 Cann et al.
5,676,648 A 10/1997 Henley
5,683,971 A 11/1997 Rose et al.
5,697,920 A 12/1997 Gibbons
5,707,383 A 1/1998 Bays
5,713,785 A 2/1998 Nishio
5,735,833 A 4/1998 Olson
5,755,751 A 5/1998 Eckhouse
5,759,185 A 6/1998 Grinberg
5,762,640 A 6/1998 Kajiwara et al.
5,779,519 A 7/1998 Oliver
5,800,446 A 9/1998 Banuchi
5,807,353 A 9/1998 Schmitz
5,810,842 A 9/1998 Di Fiore
5,813,416 A 9/1998 Rudolph
5,817,050 A 10/1998 Klein
5,817,089 A 10/1998 Tankovich et al.
5,834,510 A 11/1998 Yu et al.
5,846,215 A 12/1998 Zygmont
5,848,998 A 12/1998 Marasco, Jr.
5,857,995 A 1/1999 Thomas et al.
5,861,142 A 1/1999 Schick
5,873,881 A 2/1999 McEwen et al.
5,879,323 A 3/1999 Henley
5,879,376 A 3/1999 Miller
5,882,201 A 3/1999 Salem
5,885,260 A 3/1999 Mehl, Sr. et al.
5,908,401 A 6/1999 Henley
5,911,223 A 6/1999 Weaver et al.

(56) References Cited

U.S. PATENT DOCUMENTS

| | | | |
|---|---|---|---|
| 5,919,152 | A | 7/1999 | Zygmont |
| 5,919,479 | A | 7/1999 | Zhang et al. |
| 5,954,730 | A | 9/1999 | Bernabei |
| 5,971,999 | A | 10/1999 | Naldoni |
| 5,980,555 | A | 11/1999 | Barbut et al. |
| 6,019,749 | A | 2/2000 | Fields et al. |
| 6,023,639 | A | 2/2000 | Hakky et al. |
| 6,024,733 | A | 2/2000 | Eggers et al. |
| 6,027,402 | A | 2/2000 | Oliver |
| 6,027,495 | A | 2/2000 | Miller |
| 6,032,071 | A | 2/2000 | Binder |
| 6,036,684 | A | 3/2000 | Tankovich et al. |
| 6,039,745 | A | 3/2000 | Di Fiore et al. |
| 6,042,552 | A | 3/2000 | Cornier |
| D425,241 | S | 5/2000 | Nishizawa et al. |
| 6,074,382 | A | 6/2000 | Asah et al. |
| 6,080,165 | A | 6/2000 | DeJacma |
| 6,080,166 | A | 6/2000 | McEwen et al. |
| D428,142 | S | 7/2000 | Stromblad |
| 6,090,085 | A | 7/2000 | Mehl, Sr. et al. |
| 6,093,021 | A | 7/2000 | Rainey |
| 6,113,559 | A | 9/2000 | Klopotek |
| 6,120,512 | A | 9/2000 | Bernabei |
| 6,129,701 | A | 10/2000 | Cimino |
| 6,136,008 | A | 10/2000 | Becker et al. |
| 6,139,553 | A | 10/2000 | Dotan |
| 6,139,554 | A | 10/2000 | Karkar et al. |
| 6,142,155 | A | 11/2000 | Rudolph |
| 6,149,634 | A | 11/2000 | Bernabei |
| 6,149,644 | A | 11/2000 | Xie |
| 6,159,226 | A | 12/2000 | Kim |
| 6,162,218 | A | 12/2000 | Elbrecht et al. |
| 6,162,232 | A | 12/2000 | Shadduck |
| 6,165,059 | A | 12/2000 | Parkin et al. |
| 6,174,325 | B1 | 1/2001 | Eckhouse |
| 6,176,198 | B1 | 1/2001 | Kao et al. |
| 6,183,451 | B1 | 2/2001 | Mehl, Sr. et al. |
| 6,183,483 | B1 | 2/2001 | Chang |
| 6,190,376 | B1 | 2/2001 | Asah et al. |
| 6,193,589 | B1 | 2/2001 | Khalaj |
| 6,196,982 | B1 | 3/2001 | Ball |
| 6,231,593 | B1 | 5/2001 | Meserol |
| 6,235,039 | B1 | 5/2001 | Parkin et al. |
| 6,238,275 | B1 | 5/2001 | Metcalf et al. |
| 6,241,739 | B1 | 6/2001 | Waldron |
| 6,245,347 | B1 | 6/2001 | Zhang et al. |
| 6,264,666 | B1 | 7/2001 | Coleman et al. |
| 6,269,271 | B1 | 7/2001 | Bernabei |
| 6,277,116 | B1 | 8/2001 | Utely et al. |
| 6,277,128 | B1 | 8/2001 | Muldner |
| 6,280,438 | B1 | 8/2001 | Eckhouse et al. |
| 6,283,978 | B1 | 9/2001 | Cheski et al. |
| 6,284,266 | B1 | 9/2001 | Zhang et al. |
| 6,299,620 | B1 | 10/2001 | Shadduck |
| 6,306,119 | B1 | 10/2001 | Weber et al. |
| 6,306,147 | B1 | 10/2001 | Bernabei et al. |
| 6,322,548 | B1 | 11/2001 | Payne et al. |
| 6,322,568 | B1 | 11/2001 | Bernabei et al. |
| 6,325,381 | B1 | 12/2001 | von Engelbrechten |
| 6,325,769 | B1 | 12/2001 | Klopotek |
| 6,332,886 | B1 | 12/2001 | Green et al. |
| 6,334,074 | B1 | 12/2001 | Spertell |
| 6,355,054 | B1 | 3/2002 | Neuberger |
| 6,368,333 | B2 | 4/2002 | Bernabei et al. |
| 6,383,177 | B1 | 5/2002 | Balle-Petersen et al. |
| 6,387,089 | B1 | 5/2002 | Kreindel et al. |
| 6,387,103 | B2 | 5/2002 | Shadduck |
| 6,401,289 | B1 | 6/2002 | Herbert |
| 6,409,736 | B1 | 6/2002 | Bernabei |
| 6,410,599 | B1 | 6/2002 | Johnson |
| RE37,796 | E | 7/2002 | Henley |
| 6,414,032 | B1 | 7/2002 | Johnson |
| 6,420,431 | B1 | 7/2002 | Johnson |
| 6,423,078 | B1 | 7/2002 | Bays et al. |
| 6,423,750 | B1 | 7/2002 | Johnson |
| 6,432,113 | B1 | 8/2002 | Parkin et al. |
| 6,432,114 | B1 | 8/2002 | Rosso |
| 6,458,109 | B1 | 10/2002 | Henley et al. |
| 6,471,712 | B2 | 10/2002 | Burres |
| 6,477,410 | B1 | 11/2002 | Henley et al. |
| 6,482,212 | B1 | 11/2002 | Bernabei et al. |
| 6,488,646 | B1 | 12/2002 | Zygmont |
| 6,494,856 | B1 | 12/2002 | Zygmont |
| 6,500,183 | B1 | 12/2002 | Waldron |
| 6,503,256 | B2 | 1/2003 | Parkin et al. |
| 6,508,813 | B1 | 1/2003 | Altshuler |
| 6,511,486 | B2 | 1/2003 | Mercier et al. |
| 6,514,243 | B1 | 2/2003 | Eckhouse et al. |
| 6,514,262 | B1 | 2/2003 | Di Fiore et al. |
| 6,514,278 | B1 | 2/2003 | Hibst et al. |
| 6,518,538 | B2 | 2/2003 | Bernabei |
| 6,520,931 | B2 | 2/2003 | Suh |
| D472,136 | S | 3/2003 | Hermann |
| 6,527,716 | B1 | 3/2003 | Eppstein |
| 6,527,783 | B1 | 3/2003 | Ignon |
| 6,533,776 | B2 | 3/2003 | Asah et al. |
| 6,535,761 | B2 | 3/2003 | Bernabei |
| 6,537,242 | B1 | 3/2003 | Palmer |
| 6,540,757 | B1 | 4/2003 | Hruska et al. |
| 6,546,281 | B1 | 4/2003 | Zhang et al. |
| 6,562,013 | B1 | 5/2003 | Marasco, Jr. |
| 6,562,050 | B1 | 5/2003 | Owen |
| 6,564,093 | B1 | 5/2003 | Ostrow et al. |
| 6,565,535 | B2 | 5/2003 | Zaias et al. |
| 6,569,157 | B1 | 5/2003 | Shain et al. |
| 6,582,442 | B2 | 6/2003 | Simon et al. |
| 6,587,730 | B2 | 7/2003 | Bernabei |
| 6,589,218 | B2 | 7/2003 | Garcia |
| 6,592,595 | B1 | 7/2003 | Mallett et al. |
| 6,595,934 | B1 | 7/2003 | Hissong et al. |
| 6,611,706 | B2 | 8/2003 | Avrahami et al. |
| 6,626,445 | B2 | 9/2003 | Murphy et al. |
| 6,629,927 | B1 | 10/2003 | Mesaros et al. |
| 6,629,971 | B2 | 10/2003 | McDaniel |
| 6,629,974 | B2 | 10/2003 | Penny et al. |
| 6,629,983 | B1 | 10/2003 | Ignon |
| 6,635,035 | B1 | 10/2003 | Marasco et al. |
| 6,641,591 | B1 | 11/2003 | Shadduck |
| 6,645,184 | B1 | 11/2003 | Zelickson et al. |
| 6,652,888 | B2 | 11/2003 | Rhoades |
| 6,666,874 | B2 | 12/2003 | Heitzmann et al. |
| 6,673,081 | B1 | 1/2004 | Tavger et al. |
| 6,673,082 | B2 | 1/2004 | Mallett et al. |
| D486,915 | S | 2/2004 | Warschewske et al. |
| 6,685,853 | B1 | 2/2004 | Angelopoulous et al. |
| 6,687,537 | B2 | 2/2004 | Bernabei |
| 6,689,380 | B1 | 2/2004 | Marchitto et al. |
| 6,695,853 | B2 | 2/2004 | Karasiuk |
| 6,699,237 | B2 | 3/2004 | Weber et al. |
| 6,712,805 | B2 | 3/2004 | Weimann |
| 6,726,673 | B1 | 4/2004 | Zhang et al. |
| D490,561 | S | 5/2004 | Angeletta |
| 6,735,470 | B2 | 5/2004 | Henley et al. |
| 6,743,211 | B1 | 6/2004 | Prausnitz et al. |
| 6,743,215 | B2 | 6/2004 | Bernabei |
| 6,764,493 | B1 | 7/2004 | Weber et al. |
| 6,780,426 | B2 | 8/2004 | Zhang et al. |
| D496,101 | S | 9/2004 | Davison |
| 6,800,083 | B2 | 10/2004 | Hiblar et al. |
| 6,800,849 | B2 | 10/2004 | Staats |
| D499,207 | S | 11/2004 | Angeletta |
| D499,841 | S | 12/2004 | Angeletta |
| D502,288 | S | 2/2005 | Longoria |
| D502,289 | S | 2/2005 | Longoria |
| D502,569 | S | 3/2005 | Longoria |
| 6,869,611 | B1 | 3/2005 | Kligman et al. |
| 6,878,144 | B2 | 4/2005 | Altshuler et al. |
| 6,887,260 | B1 | 5/2005 | McDaniel |
| 6,905,487 | B2 | 6/2005 | Zimmerman |
| 6,911,031 | B2 | 6/2005 | Muldner |
| 6,926,681 | B1 | 8/2005 | Ramey et al. |
| 6,938,805 | B2 | 9/2005 | Brincat |
| 6,942,649 | B2 | 9/2005 | Ignon et al. |
| 6,960,206 | B2 | 11/2005 | Keane |

(56) References Cited

U.S. PATENT DOCUMENTS

| | | | |
|---|---|---|---|
| 6,980,448 | B2 | 12/2005 | Foss et al. |
| 7,001,355 | B2 | 2/2006 | Nunomura et al. |
| 7,004,933 | B2 | 2/2006 | McDaniel |
| D517,699 | S | 3/2006 | Lansohn |
| 7,031,805 | B2 | 4/2006 | Lee et al. |
| 7,044,938 | B2 | 5/2006 | La Bianco et al. |
| 7,051,907 | B2 | 5/2006 | Brincat |
| 7,052,503 | B2 | 5/2006 | Bernabei |
| D522,360 | S | 6/2006 | Caserta et al. |
| 7,062,317 | B2 | 6/2006 | Avrahami et al. |
| 7,069,073 | B2 | 6/2006 | Henley et al. |
| 7,070,488 | B2 | 7/2006 | Suissa et al. |
| 7,083,580 | B2 | 8/2006 | Bernabei |
| 7,087,036 | B2 | 8/2006 | Busby et al. |
| 7,087,063 | B2 | 8/2006 | Carson et al. |
| 7,094,252 | B2 | 8/2006 | Koop |
| 7,108,689 | B2 | 9/2006 | Eckhouse et al. |
| 7,115,275 | B2 | 10/2006 | Clarot et al. |
| 7,118,563 | B2 | 10/2006 | Weckwerth et al. |
| 7,122,029 | B2 | 10/2006 | Koop et al. |
| 7,135,011 | B2 | 11/2006 | Powers et al. |
| D533,962 | S | 12/2006 | Angeletta |
| 7,153,311 | B2 | 12/2006 | Chung |
| 7,166,086 | B2 | 1/2007 | Haider et al. |
| D536,481 | S | 2/2007 | Angeletta |
| 7,172,572 | B2 | 2/2007 | Diamond et al. |
| 7,189,230 | B2 | 3/2007 | Knowlton |
| 7,197,359 | B1 | 3/2007 | Tokudome et al. |
| 7,198,623 | B2 | 4/2007 | Fischer et al. |
| 7,201,765 | B2 | 4/2007 | McDaniel |
| D545,207 | S | 6/2007 | De Baschmakoff |
| 7,232,431 | B1 | 6/2007 | Weimann |
| 7,232,444 | B2 | 6/2007 | Chang |
| 7,241,208 | B2 | 7/2007 | Suissa et al. |
| 7,250,045 | B2 | 7/2007 | Island et al. |
| D548,341 | S | 8/2007 | Ohta et al. |
| D548,843 | S | 8/2007 | Kertz |
| D553,005 | S | 10/2007 | Py et al. |
| 7,276,051 | B1 | 10/2007 | Henley et al. |
| 7,293,930 | B2 | 11/2007 | Chuang |
| D557,611 | S | 12/2007 | Ingemarsson |
| 7,314,326 | B2 | 1/2008 | Rosenberg |
| 7,316,657 | B2 | 1/2008 | Kleinhenz et al. |
| 7,316,671 | B2 | 1/2008 | Lastovich et al. |
| 7,318,828 | B1 | 1/2008 | Revivo |
| 7,320,691 | B2 | 1/2008 | Pilcher et al. |
| 7,320,801 | B2 | 1/2008 | Kelly |
| 7,326,199 | B2 | 2/2008 | MacFarland et al. |
| 7,329,252 | B1 | 2/2008 | Yamazaki et al. |
| 7,354,423 | B2 | 4/2008 | Zelickson et al. |
| 7,364,565 | B2 | 4/2008 | Freeman |
| D568,473 | S | 5/2008 | Ashiwa et al. |
| 7,367,981 | B2 | 5/2008 | Bernaz |
| 7,384,405 | B2 | 6/2008 | Rhoades |
| 7,422,567 | B2 | 9/2008 | Lastovich et al. |
| 7,427,273 | B2 | 9/2008 | Mitsui |
| 7,440,798 | B2 | 10/2008 | Redding, Jr. |
| 7,458,944 | B2 | 12/2008 | Liste et al. |
| D584,151 | S | 1/2009 | Murphy |
| 7,476,205 | B2 | 1/2009 | Erdmann |
| 7,477,938 | B2 | 1/2009 | Sun et al. |
| 7,482,314 | B2 | 1/2009 | Grimes et al. |
| 7,485,125 | B2 | 2/2009 | Sjostrom |
| 7,489,989 | B2 | 2/2009 | Sukhanov et al. |
| 7,494,503 | B2 | 2/2009 | McDaniel |
| 7,507,228 | B2 | 3/2009 | Sun et al. |
| 7,572,238 | B2 | 8/2009 | Rhoades |
| 7,582,067 | B2 | 9/2009 | Van Acker |
| 7,597,900 | B2 | 10/2009 | Zimmer et al. |
| 7,597,901 | B2 | 10/2009 | Clarot et al. |
| 7,607,972 | B2 | 10/2009 | Groman |
| 7,658,742 | B2 | 2/2010 | Karasiuk |
| 7,678,120 | B2 | 3/2010 | Shadduck |
| 7,730,979 | B2 | 6/2010 | Kahrig |
| 7,731,570 | B2 | 6/2010 | Groman |
| 7,740,651 | B2 | 6/2010 | Barak et al. |
| 7,744,582 | B2 | 6/2010 | Sadowski et al. |
| 7,749,260 | B2 | 7/2010 | Da Silva et al. |
| 7,758,537 | B1 | 7/2010 | Brunell et al. |
| 7,771,374 | B2 | 8/2010 | Slatkine |
| 7,780,652 | B2 | 8/2010 | MacFarland et al. |
| 7,789,886 | B2 | 9/2010 | Shadduck |
| D625,198 | S | 10/2010 | Hall |
| 7,814,915 | B2 | 10/2010 | Davenport et al. |
| 7,837,695 | B2 | 11/2010 | Hart et al. |
| 7,857,806 | B2 | 12/2010 | Karpowicz et al. |
| 7,862,564 | B2 | 1/2011 | Goble |
| 7,901,373 | B2 | 3/2011 | Tavger |
| 7,927,188 | B2 | 4/2011 | Groman |
| 7,951,156 | B2 | 5/2011 | Karasiuk |
| D639,164 | S | 6/2011 | Walsh |
| 7,981,111 | B2 | 7/2011 | Grove et al. |
| 7,981,112 | B1 | 7/2011 | Neev |
| 7,993,333 | B2 | 8/2011 | Oral et al. |
| 8,025,669 | B1 | 9/2011 | David et al. |
| RE42,960 | E | 11/2011 | Waldron |
| 8,048,064 | B2 | 11/2011 | Hwang et al. |
| 8,048,089 | B2 | 11/2011 | Ignon et al. |
| 8,066,716 | B2 | 11/2011 | Shadduck |
| 8,088,085 | B2 | 1/2012 | Thiebaut et al. |
| 8,105,295 | B2 | 1/2012 | Blott et al. |
| 8,128,638 | B2 | 3/2012 | Karasiuk et al. |
| 8,135,475 | B2 | 3/2012 | Kreindel et al. |
| 8,182,473 | B2 | 5/2012 | Altshuler et al. |
| D664,254 | S | 7/2012 | Yokoyama et al. |
| 8,221,437 | B2 | 7/2012 | Waldron et al. |
| 8,226,663 | B2 | 7/2012 | Remsburg et al. |
| 8,231,292 | B2 | 7/2012 | Rabe et al. |
| 8,236,008 | B2 | 8/2012 | Boone, III et al. |
| 8,236,036 | B1 | 8/2012 | Frost |
| 8,241,094 | B2 | 8/2012 | Groman |
| 8,273,080 | B2 | 9/2012 | Mehta |
| 8,276,592 | B2 | 10/2012 | Davenport et al. |
| 8,277,287 | B2 | 10/2012 | Hart |
| 8,282,630 | B2 | 10/2012 | Neev |
| 8,313,480 | B2 | 11/2012 | Neev |
| 8,317,781 | B2 | 11/2012 | Owens et al. |
| 8,323,253 | B2 | 12/2012 | Hantash et al. |
| 8,337,513 | B2 | 12/2012 | Shadduck |
| 8,343,116 | B2 | 1/2013 | Ignon et al. |
| 8,360,826 | B2 | 1/2013 | Groman |
| D676,764 | S | 2/2013 | Moore et al. |
| D678,783 | S | 3/2013 | Wilcox et al. |
| 8,398,621 | B2 | 3/2013 | Beerwerth et al. |
| D680,437 | S | 4/2013 | Bartolo et al. |
| 8,430,104 | B2 | 4/2013 | Hennings et al. |
| 8,435,234 | B2 | 5/2013 | Chan et al. |
| 8,475,507 | B2 | 7/2013 | Dewey et al. |
| 8,478,396 | B2 | 7/2013 | Tsao et al. |
| 8,480,721 | B2 | 7/2013 | Owens et al. |
| 8,496,654 | B2 | 7/2013 | Adanny et al. |
| 8,496,695 | B2 | 7/2013 | Kang et al. |
| 8,535,299 | B2 | 9/2013 | Giovannoli |
| 8,545,419 | B2 | 10/2013 | Kim |
| 8,545,489 | B2 | 10/2013 | Giovannoli |
| 8,551,104 | B2 | 10/2013 | Weckwerth et al. |
| 8,562,626 | B2 | 10/2013 | Sabir et al. |
| 8,573,874 | B2 | 11/2013 | Neuner |
| 8,579,916 | B2 | 11/2013 | Cheney |
| 8,597,284 | B2 | 12/2013 | Castro |
| D697,404 | S | 1/2014 | Johnson et al. |
| 8,632,378 | B2 | 1/2014 | Groman |
| D699,367 | S | 2/2014 | Lee et al. |
| 8,656,931 | B2 | 2/2014 | Davenport et al. |
| 8,668,552 | B2 | 3/2014 | Groman |
| 8,679,039 | B2 | 3/2014 | Tieu et al. |
| 8,700,176 | B2 | 4/2014 | Azar et al. |
| 8,702,691 | B2 | 4/2014 | Weber et al. |
| 8,702,771 | B1 | 4/2014 | Frost |
| 8,721,662 | B2 | 5/2014 | Karasiuk |
| 8,728,064 | B2 | 5/2014 | Schomacker et al. |
| 8,740,917 | B2 | 6/2014 | Pilcher et al. |
| D709,617 | S | 7/2014 | Iliesco de Grimaldi et al. |
| 8,814,836 | B2 | 8/2014 | Ignon et al. |

(56) References Cited

U.S. PATENT DOCUMENTS

| | | | |
|---|---|---|---|
| 8,818,500 | B2 | 8/2014 | Duquet et al. |
| 8,821,940 | B2 | 9/2014 | Harris et al. |
| 8,834,933 | B2 | 9/2014 | Harris et al. |
| 8,858,570 | B2 | 10/2014 | Chang |
| 8,939,669 | B2 | 1/2015 | Le et al. |
| D722,172 | S | 2/2015 | Amemiya et al. |
| 8,945,104 | B2 | 2/2015 | Boone, III et al. |
| 8,945,109 | B2 | 2/2015 | Mehta |
| 8,974,442 | B1 | 3/2015 | Boss, Jr. |
| 9,017,391 | B2 | 4/2015 | McDaniel |
| 9,017,392 | B2 | 4/2015 | Owens et al. |
| 9,044,582 | B2 | 6/2015 | Chang et al. |
| 9,050,133 | B1 | 6/2015 | Boone, III et al. |
| 9,050,156 | B2 | 6/2015 | Groman |
| 9,056,193 | B2 | 6/2015 | Ignon et al. |
| D734,154 | S | 7/2015 | Johnson et al. |
| 9,072,521 | B2 | 7/2015 | Levi et al. |
| 9,072,533 | B2 | 7/2015 | Liu et al. |
| 9,072,892 | B2 | 7/2015 | Owens et al. |
| 9,084,587 | B2 | 7/2015 | Eckhouse et al. |
| 9,149,322 | B2 | 10/2015 | Knowlton |
| D743,269 | S | 11/2015 | Pape |
| D743,558 | S | 11/2015 | Kim et al. |
| 9,186,490 | B2 | 11/2015 | Chang et al. |
| 9,227,044 | B2 | 1/2016 | Bansal et al. |
| 9,227,082 | B2 | 1/2016 | McDaniel |
| 9,233,207 | B2 | 1/2016 | Polyakov et al. |
| 9,271,755 | B2 | 3/2016 | Luzon et al. |
| 9,278,230 | B2 | 3/2016 | Levin et al. |
| 9,283,037 | B2 | 3/2016 | Bragagna et al. |
| 9,314,302 | B2 | 4/2016 | Dougal |
| 9,351,792 | B2 | 5/2016 | Manstein et al. |
| 9,351,794 | B2 | 5/2016 | Suckewer et al. |
| 9,375,281 | B2 | 6/2016 | Moench et al. |
| 9,421,260 | B2 | 8/2016 | Harris et al. |
| 9,421,261 | B2 | 8/2016 | Harris et al. |
| D765,512 | S | 9/2016 | Joulia |
| 9,439,964 | B2 | 9/2016 | Harris et al. |
| 9,440,093 | B2 | 9/2016 | Homer |
| 9,452,013 | B2 | 9/2016 | Manstein |
| 9,468,464 | B2 | 10/2016 | Shadduck |
| 9,474,886 | B2 | 10/2016 | Ignon et al. |
| D772,481 | S | 11/2016 | Paquet |
| 9,480,836 | B2 | 11/2016 | Na |
| 9,486,615 | B2 | 11/2016 | Ignon et al. |
| 9,498,610 | B2 | 11/2016 | Ignon et al. |
| 9,517,085 | B2 | 12/2016 | Karasiuk |
| 9,522,287 | B2 | 12/2016 | Owens et al. |
| 9,550,052 | B2 | 1/2017 | Ignon et al. |
| 9,566,088 | B2 | 2/2017 | Ignon et al. |
| 9,566,454 | B2 | 2/2017 | Barthe et al. |
| 9,572,880 | B2 | 2/2017 | Harris et al. |
| 9,597,527 | B2 | 3/2017 | Buchholz et al. |
| D782,881 | S | 4/2017 | Seiders et al. |
| D787,054 | S | 5/2017 | Rini et al. |
| 9,636,521 | B2 | 5/2017 | Isserow et al. |
| 9,636,522 | B2 | 5/2017 | Oversluizen et al. |
| 9,642,997 | B2 | 5/2017 | Ignon et al. |
| 9,662,482 | B2 | 5/2017 | Ignon et al. |
| 9,669,233 | B2 | 6/2017 | Quisenberry et al. |
| 9,675,817 | B2 | 6/2017 | Isserow et al. |
| 9,694,199 | B2 | 7/2017 | Duquet et al. |
| 9,700,684 | B2 | 7/2017 | Vlodaver et al. |
| 9,731,053 | B2 | 8/2017 | Alai |
| 9,744,315 | B1 | 8/2017 | Levi |
| 9,775,645 | B2 | 10/2017 | Boone, III |
| 9,775,646 | B2 | 10/2017 | Shadduck |
| 9,775,976 | B2 | 10/2017 | Grez |
| 9,814,485 | B2 | 11/2017 | Pratt et al. |
| 9,814,647 | B2 | 11/2017 | Ajiki |
| 9,814,868 | B2 | 11/2017 | Ignon et al. |
| 9,814,906 | B2 | 11/2017 | McDaniel |
| 9,833,261 | B2 | 12/2017 | Boone, III et al. |
| 9,861,442 | B2 | 1/2018 | Tankovich et al. |
| D811,225 | S | 2/2018 | Newson |
| D811,381 | S | 2/2018 | Morohoshi et al. |
| 9,918,727 | B1 | 3/2018 | Boone et al. |
| 9,949,552 | B2 | 4/2018 | Rabe et al. |
| 9,950,147 | B2 | 4/2018 | Mehta |
| 9,955,769 | B2 | 5/2018 | Rabe et al. |
| 9,962,220 | B2 | 5/2018 | Domankevitz |
| 9,968,800 | B2 | 5/2018 | Anderson et al. |
| 10,004,919 | B2 | 6/2018 | Lemmens et al. |
| D822,845 | S | 7/2018 | Shimobayashi et al. |
| 10,010,445 | B2 | 7/2018 | Isserow et al. |
| 10,022,289 | B2 | 7/2018 | Ajiki et al. |
| 10,035,007 | B2 | 7/2018 | Ignon et al. |
| D825,763 | S | 8/2018 | Lim et al. |
| 10,052,467 | B2 | 8/2018 | Bansal et al. |
| D829,333 | S | 9/2018 | Shin et al. |
| 10,076,354 | B2 | 9/2018 | Knowlton |
| 10,076,646 | B2 | 9/2018 | Casasanta, III et al. |
| 10,080,581 | B2 | 9/2018 | Knowlton |
| D829,921 | S | 10/2018 | Xiong |
| 10,092,478 | B1 | 10/2018 | Amit |
| 10,105,191 | B2 | 10/2018 | Blanco et al. |
| D833,283 | S | 11/2018 | Rock |
| 10,130,390 | B1 | 11/2018 | Hart et al. |
| 10,130,827 | B2 | 11/2018 | Buchholz et al. |
| D836,781 | S | 12/2018 | Meurer et al. |
| 10,149,969 | B2 | 12/2018 | Grez et al. |
| 10,149,984 | B2 | 12/2018 | Modi et al. |
| 10,172,644 | B2 | 1/2019 | Ignon et al. |
| 10,179,229 | B2 | 1/2019 | Ignon et al. |
| 10,183,183 | B2 | 1/2019 | Burdette |
| 10,188,193 | B2 | 1/2019 | Rabe et al. |
| 10,206,743 | B2 | 2/2019 | Tankovich et al. |
| 10,207,034 | B2 | 2/2019 | Collins |
| 10,220,122 | B2 | 3/2019 | Clark, III et al. |
| 10,238,812 | B2 | 3/2019 | Ignon |
| 10,238,849 | B2 | 3/2019 | Britva et al. |
| 10,251,675 | B2 | 4/2019 | Ignon et al. |
| 10,252,044 | B2 | 4/2019 | Bock |
| 10,271,900 | B2 | 4/2019 | Marchitto et al. |
| 10,272,258 | B2 | 4/2019 | Quisenberry et al. |
| D851,759 | S | 6/2019 | Jones et al. |
| 10,307,330 | B1 | 6/2019 | Sedic |
| 10,308,378 | B2 | 6/2019 | Goodwin et al. |
| 10,314,378 | B2 | 6/2019 | Rabe et al. |
| 10,321,948 | B2 | 6/2019 | Knowlton |
| 10,322,233 | B2 | 6/2019 | Hanson et al. |
| 10,328,277 | B2 | 6/2019 | Modi et al. |
| D852,962 | S | 7/2019 | Chang |
| 10,334,933 | B2 | 7/2019 | Decaux et al. |
| 10,335,191 | B2 | 7/2019 | Knowlton |
| 10,357,641 | B2 | 7/2019 | Ignon et al. |
| 10,357,642 | B2 | 7/2019 | Ignon et al. |
| 10,369,073 | B2 | 8/2019 | Rosario et al. |
| 10,413,359 | B2 | 9/2019 | Felsenstein et al. |
| D861,913 | S | 10/2019 | Stamm et al. |
| 10,456,197 | B2 | 10/2019 | Felsenstein et al. |
| 10,456,321 | B2 | 10/2019 | Shadduck |
| 10,456,567 | B2 | 10/2019 | Streeter |
| D867,587 | S | 11/2019 | Holtz |
| 10,463,429 | B2 | 11/2019 | Deem et al. |
| 10,471,274 | B2 | 11/2019 | Liu et al. |
| 10,485,983 | B1 | 11/2019 | Boone, III et al. |
| D868,981 | S | 12/2019 | Salamon et al. |
| D873,430 | S | 1/2020 | Accolla |
| D873,481 | S | 1/2020 | Larkin |
| 10,524,835 | B2 | 1/2020 | Shadduck et al. |
| 10,537,304 | B2 | 1/2020 | Barthe et al. |
| 10,537,640 | B2 | 1/2020 | Harris et al. |
| 10,556,096 | B2 | 2/2020 | Ignon et al. |
| 10,556,097 | B2 | 2/2020 | Ignon et al. |
| 10,583,037 | B2 | 3/2020 | Isserow et al. |
| D886,370 | S | 6/2020 | Soutelo Gomes |
| D886,372 | S | 6/2020 | Weinrich |
| D887,571 | S | 6/2020 | Liu |
| 10,667,985 | B2 | 6/2020 | Decaux et al. |
| 10,675,481 | B1 | 6/2020 | Tankovich |
| 10,688,290 | B1 | 6/2020 | Yuval |
| 10,702,328 | B2 | 7/2020 | Slatkine et al. |
| 10,716,924 | B2 | 7/2020 | Knowlton |

(56) References Cited

U.S. PATENT DOCUMENTS

| | | | |
|---|---|---|---|
| D893,024 | S | 8/2020 | Whiteside |
| 10,736,653 | B2 | 8/2020 | Knowlton |
| 10,737,080 | B2 | 8/2020 | Patterson |
| 10,758,261 | B2 | 9/2020 | Richardson |
| 10,772,658 | B2 | 9/2020 | Knowlton |
| 10,792,382 | B2 | 10/2020 | Rafko |
| 10,799,285 | B2 | 10/2020 | Mulholland |
| 10,799,430 | B2 | 10/2020 | Danto |
| 10,813,694 | B2 | 10/2020 | Johnson et al. |
| 10,835,287 | B2 | 11/2020 | Shadduck et al. |
| 10,835,726 | B2 | 11/2020 | Redding, Jr. |
| D903,889 | S | 12/2020 | Luo et al. |
| 10,850,095 | B2 | 12/2020 | Ebbers et al. |
| 10,856,900 | B2 | 12/2020 | Knowlton |
| 10,860,026 | B2 | 12/2020 | Nguyen et al. |
| 10,874,579 | B1 | 12/2020 | Rembert |
| D908,282 | S | 1/2021 | Kim |
| 10,893,907 | B2 | 1/2021 | Kim |
| 10,912,428 | B2 | 2/2021 | Daffer |
| 10,918,190 | B2 | 2/2021 | Laudati |
| 10,946,191 | B2 | 3/2021 | Cazares Delgadillo |
| 10,952,811 | B2 | 3/2021 | Blanco et al. |
| 10,952,907 | B1 | 3/2021 | Carver |
| D917,290 | S | 4/2021 | Bravman et al. |
| 10,980,592 | B2 | 4/2021 | Horton et al. |
| 10,993,743 | B2 | 5/2021 | Ignon et al. |
| 11,020,577 | B2 | 6/2021 | Ignon et al. |
| 11,045,661 | B2 | 6/2021 | Oversluizen et al. |
| D927,008 | S | 8/2021 | Rappaport |
| D928,977 | S | 8/2021 | Dijkstra |
| 11,083,515 | B2 | 8/2021 | Slatkine et al. |
| 11,123,039 | B2 | 9/2021 | Barthe et al. |
| 11,141,761 | B2 | 10/2021 | Connelly et al. |
| 11,154,723 | B2 | 10/2021 | Lee |
| 11,172,978 | B2 | 11/2021 | Wootten et al. |
| 11,202,657 | B2 | 12/2021 | Ignon et al. |
| 11,213,321 | B2 | 1/2022 | Ignon et al. |
| 11,224,728 | B2 | 1/2022 | Ignon et al. |
| 11,241,357 | B2 | 2/2022 | Ignon et al. |
| 11,247,039 | B2 | 2/2022 | Schwarz |
| 11,278,101 | B2 | 3/2022 | Jeannin et al. |
| 11,291,474 | B2 | 4/2022 | Nicolas et al. |
| 11,291,498 | B2 | 4/2022 | Slatkine et al. |
| 11,311,721 | B2 | 4/2022 | Ebbers et al. |
| 11,337,745 | B2 | 5/2022 | Kim |
| 11,337,755 | B2 | 5/2022 | Hancock et al. |
| 11,351,063 | B2 | 6/2022 | Locke et al. |
| 11,419,678 | B2 | 8/2022 | Deem et al. |
| D964,581 | S | 9/2022 | Guo |
| 11,446,477 | B2 | 9/2022 | Ignon et al. |
| 11,452,852 | B2 | 9/2022 | Quan et al. |
| 11,452,883 | B1 | 9/2022 | Marchese et al. |
| 11,497,553 | B2 | 11/2022 | Reinhard et al. |
| 11,504,148 | B2 | 11/2022 | Friend |
| 11,517,350 | B2 | 12/2022 | Ignon et al. |
| 11,540,882 | B2 | 1/2023 | Masotti et al. |
| 11,547,840 | B2 | 1/2023 | Ignon et al. |
| D979,782 | S | 2/2023 | Sung et al. |
| 11,590,345 | B2 | 2/2023 | Danitz et al. |
| 11,602,629 | B2 | 3/2023 | Schwarz et al. |
| 11,612,726 | B2 | 3/2023 | Ignon et al. |
| D994,134 | S | 8/2023 | Lim |
| 11,717,326 | B2 | 8/2023 | Ignon et al. |
| D998,143 | S | 9/2023 | Nagao et al. |
| 11,744,999 | B2 | 9/2023 | Ignon et al. |
| 11,806,495 | B2 | 11/2023 | Ignon et al. |
| D1,011,541 | S | 1/2024 | Yu |
| 11,865,287 | B2 | 1/2024 | Ignon et al. |
| 11,883,621 | B2 | 1/2024 | Ignon et al. |
| 11,903,615 | B2 | 2/2024 | Ignon et al. |
| D1,016,615 | S | 3/2024 | Rozporka et al. |
| 11,925,780 | B2 | 3/2024 | Ignon et al. |
| 2001/0023351 | A1 | 9/2001 | Eilers |
| 2001/0037118 | A1 | 11/2001 | Shadduck |
| 2001/0049511 | A1 | 12/2001 | Coleman et al. |
| 2002/0016601 | A1 | 2/2002 | Shadduck |
| 2002/0040199 | A1 | 4/2002 | Klopotek |
| 2002/0041891 | A1 | 4/2002 | Cheski |
| 2002/0058952 | A1 | 5/2002 | Weber et al. |
| 2002/0099356 | A1 | 7/2002 | Unger et al. |
| 2002/0107527 | A1 | 8/2002 | Burres |
| 2002/0128663 | A1 | 9/2002 | Mercier et al. |
| 2002/0133110 | A1 | 9/2002 | Citow |
| 2002/0133176 | A1 | 9/2002 | Parkin et al. |
| 2002/0151826 | A1 | 10/2002 | Ramey et al. |
| 2002/0151908 | A1 | 10/2002 | Mallett, Sr. et al. |
| 2002/0162863 | A1 | 11/2002 | Brincat |
| 2002/0188261 | A1 | 12/2002 | Hruska |
| 2002/0198488 | A1 | 12/2002 | Yao |
| 2003/0012415 | A1 | 1/2003 | Cossel |
| 2003/0018252 | A1 | 1/2003 | Duchon et al. |
| 2003/0060834 | A1 | 3/2003 | Muldner |
| 2003/0093040 | A1 | 5/2003 | Mikszta et al. |
| 2003/0093089 | A1 | 5/2003 | Greenberg |
| 2003/0097139 | A1 | 5/2003 | Karasiuk |
| 2003/0135388 | A1 | 7/2003 | Martucci et al. |
| 2003/0167032 | A1 | 9/2003 | Ignon et al. |
| 2003/0187462 | A1 | 10/2003 | Chang |
| 2003/0208159 | A1 | 11/2003 | Ignon et al. |
| 2003/0212127 | A1 | 11/2003 | Glassman et al. |
| 2003/0212415 | A1 | 11/2003 | Karasiuk |
| 2004/0005349 | A1 | 1/2004 | Neev |
| 2004/0010222 | A1 | 1/2004 | Nunomura et al. |
| 2004/0010269 | A1 | 1/2004 | Grimes et al. |
| 2004/0015139 | A1 | 1/2004 | La Bianco |
| 2004/0051368 | A1 | 3/2004 | Caputo et al. |
| 2004/0087972 | A1 | 5/2004 | Mulholland et al. |
| 2004/0092895 | A1 | 5/2004 | Harmon |
| 2004/0092959 | A1 | 5/2004 | Bernaz |
| 2004/0097967 | A1 | 5/2004 | Ignon |
| 2004/0122447 | A1 | 6/2004 | Harmon et al. |
| 2004/0127914 | A1 | 7/2004 | Chung |
| 2004/0138680 | A1 | 7/2004 | Twitchell et al. |
| 2004/0162565 | A1 | 8/2004 | Carson et al. |
| 2004/0166172 | A1 | 8/2004 | Rosati et al. |
| 2004/0176823 | A1 | 9/2004 | Island et al. |
| 2004/0210167 | A1 | 10/2004 | Webster |
| 2004/0210280 | A1 | 10/2004 | Liedtke |
| 2004/0219179 | A1 | 11/2004 | McDaniel |
| 2004/0229295 | A1 | 11/2004 | Marchitto et al. |
| 2004/0236291 | A1 | 11/2004 | Zelickson et al. |
| 2004/0236375 | A1 | 11/2004 | Redding, Jr. |
| 2004/0243149 | A1 | 12/2004 | Lee, Jr. |
| 2004/0254587 | A1 | 12/2004 | Park |
| 2004/0267285 | A1 | 12/2004 | Chang |
| 2005/0015077 | A1 | 1/2005 | Kuklin et al. |
| 2005/0037034 | A1 | 2/2005 | Rhoades |
| 2005/0038377 | A1 | 2/2005 | Redding, Jr. |
| 2005/0038448 | A1 | 2/2005 | Chung |
| 2005/0059940 | A1 | 3/2005 | Weber et al. |
| 2005/0065461 | A1 | 3/2005 | Redding, Jr. |
| 2005/0070977 | A1 | 3/2005 | Molina |
| 2005/0075599 | A1 | 4/2005 | Redding, Jr. |
| 2005/0080465 | A1 | 4/2005 | Zelickson et al. |
| 2005/0084509 | A1 | 4/2005 | Bernstein |
| 2005/0148958 | A1 | 7/2005 | Rucinski |
| 2005/0154333 | A1 | 7/2005 | Mulholland et al. |
| 2005/0203111 | A1 | 9/2005 | David |
| 2005/0203593 | A1 | 9/2005 | Shanks et al. |
| 2005/0209611 | A1 | 9/2005 | Greenberg |
| 2005/0245180 | A1 | 11/2005 | Suissa et al. |
| 2005/0283176 | A1 | 12/2005 | Law |
| 2006/0002960 | A1 | 1/2006 | Zoeteweij et al. |
| 2006/0015059 | A1 | 1/2006 | Redding, Jr. |
| 2006/0058714 | A1 | 3/2006 | Rhoades |
| 2006/0100567 | A1 | 5/2006 | Marchitto et al. |
| 2006/0116674 | A1 | 6/2006 | Goble et al. |
| 2006/0161178 | A1 | 7/2006 | Lee |
| 2006/0184071 | A1 | 8/2006 | Klopotek |
| 2006/0189964 | A1 | 8/2006 | Anderson |
| 2006/0191562 | A1 | 8/2006 | Numomura |
| 2006/0200099 | A1 | 9/2006 | La Bianco et al. |
| 2006/0200213 | A1 | 9/2006 | McDaniel |
| 2006/0212025 | A1 | 9/2006 | McDaniel |

(56) References Cited

U.S. PATENT DOCUMENTS

2006/0212029 A1 9/2006 Villacampa et al.
2006/0222445 A1 10/2006 Chuang
2006/0235371 A1 10/2006 Wakamatsu et al.
2006/0253078 A1 11/2006 Wu et al.
2006/0253079 A1 11/2006 McDonough et al.
2006/0253125 A1 11/2006 Ignon
2006/0264893 A1 11/2006 Sage, Jr. et al.
2006/0264926 A1 11/2006 Kochamba
2006/0269580 A1 11/2006 Cole et al.
2006/0278661 A1 12/2006 Cooper et al.
2007/0005078 A1 1/2007 Hart et al.
2007/0020321 A1 1/2007 Redding et al.
2007/0027411 A1 2/2007 Ella et al.
2007/0043382 A1 2/2007 Cheney
2007/0049901 A1 3/2007 Wu et al.
2007/0065515 A1 3/2007 Key
2007/0073327 A1 3/2007 Giovannoli
2007/0078290 A1 4/2007 Esenaliev
2007/0088245 A1 4/2007 Babaev et al.
2007/0088371 A1 4/2007 Karasiuk
2007/0093694 A1 4/2007 Fassuliotis et al.
2007/0123808 A1 5/2007 Rhoades
2007/0139630 A1 6/2007 Kleman et al.
2007/0149991 A1 6/2007 Mulholland
2007/0154502 A1 7/2007 Hattendorf et al.
2007/0156124 A1 7/2007 Ignon et al.
2007/0178121 A1 8/2007 First et al.
2007/0198031 A1 8/2007 Kellogg
2007/0232987 A1 10/2007 Diaz et al.
2007/0239079 A1 10/2007 Manstein et al.
2007/0239173 A1 10/2007 Khalaj
2007/0255355 A1 11/2007 Altshuler et al.
2007/0264625 A1 11/2007 DeBenedictis et al.
2007/0270738 A1 11/2007 Wu et al.
2008/0009802 A1 1/2008 Lambino et al.
2008/0015555 A1 1/2008 Manstein et al.
2008/0027328 A1 1/2008 Klopotek et al.
2008/0027518 A1 1/2008 Island et al.
2008/0091126 A1 4/2008 Greenburg
2008/0091179 A1 4/2008 Durkin et al.
2008/0103563 A1 5/2008 Powell
2008/0119781 A1 5/2008 King
2008/0132914 A1 6/2008 Bossard et al.
2008/0139974 A1 6/2008 Da Silva
2008/0146970 A1 6/2008 Litman et al.
2008/0154161 A1 6/2008 Abbott
2008/0154183 A1 6/2008 Baker et al.
2008/0161799 A1 7/2008 Stangenes et al.
2008/0188840 A1 8/2008 Johnson et al.
2008/0193493 A1 8/2008 Rhoades
2008/0200861 A1 8/2008 Shalev et al.
2008/0200863 A1 8/2008 Chomas et al.
2008/0208146 A1 8/2008 Brandwein et al.
2008/0208179 A1 8/2008 Chan et al.
2008/0214987 A1 9/2008 Xu
2008/0215068 A1 9/2008 Hart et al.
2008/0221548 A1 9/2008 Danenberg et al.
2008/0234626 A1 9/2008 Chelak
2008/0243039 A1 10/2008 Rhoades
2008/0287864 A1 11/2008 Rosenberg
2008/0300529 A1 12/2008 Reinstein
2008/0300552 A1 12/2008 Cichocki et al.
2009/0048557 A1 2/2009 Yeshurun et al.
2009/0053390 A1 2/2009 Sakou et al.
2009/0062815 A1 3/2009 Karasiuk et al.
2009/0099091 A1 4/2009 Hantash
2009/0099093 A1 4/2009 Hantash
2009/0118684 A1 5/2009 Da Silva et al.
2009/0124985 A1 5/2009 Hasenoehrl et al.
2009/0132012 A1 5/2009 Shanks
2009/0138026 A1 5/2009 Wu
2009/0171191 A1 7/2009 Patrick et al.
2009/0171194 A1 7/2009 Patrick et al.
2009/0177171 A1 7/2009 Ignon et al.
2009/0192442 A1 7/2009 Ignon et al.
2009/0222023 A1 9/2009 Boone, III et al.
2009/0254014 A1 10/2009 Son
2009/0299237 A1 12/2009 Rhoades
2010/0023003 A1 1/2010 Mulholland
2010/0036298 A1 2/2010 Fuster
2010/0045427 A1 2/2010 Boone, III et al.
2010/0048980 A1 2/2010 De Jong et al.
2010/0049177 A1 2/2010 Boone, III et al.
2010/0049210 A1 2/2010 Boone, III et al.
2010/0056847 A1 3/2010 De Jong et al.
2010/0063565 A1 3/2010 Beerwerth et al.
2010/0217357 A1 8/2010 Da Silva
2010/0305495 A1 12/2010 Anderson et al.
2011/0054490 A1 3/2011 Hart
2011/0060270 A1 3/2011 Eppstein
2011/0066162 A1 3/2011 Cohen
2011/0067761 A1 3/2011 King
2011/0082415 A1 4/2011 Ignon et al.
2011/0144410 A1 6/2011 Kennedy
2011/0190726 A1 8/2011 Hantash et al.
2011/0251523 A1 10/2011 Kim
2011/0264028 A1 10/2011 Ramdas et al.
2011/0270137 A1 11/2011 Goren et al.
2011/0270364 A1 11/2011 Kreindel et al.
2011/0295273 A1 12/2011 Waldron et al.
2012/0022435 A1 1/2012 Ignon et al.
2012/0041338 A1 2/2012 Chickering, III et al.
2012/0041523 A1 2/2012 Solomon et al.
2012/0109041 A1 5/2012 Munz
2012/0109043 A1 5/2012 Zhou et al.
2012/0136374 A1 5/2012 Karasiuk
2012/0171636 A1 7/2012 Groman
2012/0259252 A1 10/2012 Thorn-Leeson et al.
2012/0289885 A1 11/2012 Cottrell et al.
2012/0302929 A1 11/2012 Tkachenko
2013/0004230 A1 1/2013 Kirk, III et al.
2013/0018317 A1 1/2013 Bobroff et al.
2013/0066336 A1 3/2013 Boone, III et al.
2013/0085421 A1 4/2013 Gillespie et al.
2013/0096546 A1 4/2013 Mirkov et al.
2013/0096577 A1 4/2013 Shadduck
2013/0144207 A1 6/2013 Gonon
2013/0144280 A1 6/2013 Eckhouse et al.
2013/0158547 A1 6/2013 David
2013/0204238 A1 8/2013 Lederman et al.
2013/0226075 A1 8/2013 Hennings et al.
2013/0226269 A1 8/2013 Eckhouse et al.
2013/0261534 A1 10/2013 Niezgoda et al.
2013/0268032 A1 10/2013 Neev
2013/0296807 A1 11/2013 Lintern et al.
2013/0310906 A1 11/2013 Neev
2013/0317314 A1 11/2013 Lampson
2013/0345616 A1 12/2013 Chang
2014/0031801 A1 1/2014 Giovannoli
2014/0079686 A1 3/2014 Barman et al.
2014/0081251 A1 3/2014 Giovannoli
2014/0094718 A1 4/2014 Feldman
2014/0114234 A1 4/2014 Redding, Jr.
2014/0135798 A1 5/2014 David
2014/0234004 A1 8/2014 Thorpe et al.
2014/0243589 A1 8/2014 Rowan
2014/0316492 A1 10/2014 Min et al.
2014/0343481 A1 11/2014 Ignon
2014/0378887 A1 12/2014 Chang et al.
2015/0039060 A1 2/2015 Paulussen et al.
2015/0141877 A1 5/2015 Feldman
2015/0157496 A1 6/2015 Horton et al.
2015/0202007 A1 7/2015 Mainstein et al.
2015/0231379 A1 8/2015 Ignon et al.
2015/0272623 A1 10/2015 Ignon et al.
2015/0313993 A1 11/2015 Bock
2015/0351868 A1 12/2015 Groman
2016/0015962 A1 1/2016 Maragheh et al.
2016/0018100 A1 1/2016 Batt et al.
2016/0089525 A1 3/2016 Grez et al.
2016/0175609 A1 6/2016 Dye et al.
2016/0220849 A1 8/2016 Knowlton
2016/0235257 A1 8/2016 Daffer
2016/0250415 A1 9/2016 Yagi et al.

(56) References Cited

U.S. PATENT DOCUMENTS

2016/0256671 A1 9/2016 Ignon et al.
2016/0270850 A1 9/2016 Manstein et al.
2016/0270851 A1 9/2016 Moench et al.
2016/0287333 A1 10/2016 Morrison
2016/0324578 A1 11/2016 Manstein et al.
2017/0043150 A1 2/2017 Kim
2017/0065829 A1 3/2017 Ku
2017/0106206 A1 4/2017 Seckel
2017/0128319 A1 5/2017 Decaux et al.
2017/0157419 A1 6/2017 Jeong
2017/0196759 A1 7/2017 Palomaki et al.
2017/0209894 A1 7/2017 Sporrer
2017/0252105 A1 9/2017 Deem et al.
2017/0291007 A1 10/2017 Dubey et al.
2017/0340356 A1 11/2017 Presser et al.
2017/0343308 A1 11/2017 Wojciechowski, III et al.
2018/0008500 A1 1/2018 Anderson et al.
2018/0140329 A1 5/2018 Beijens et al.
2018/0185675 A1 7/2018 Kern et al.
2018/0310979 A1 11/2018 Peled et al.
2018/0326191 A1 11/2018 Bansal et al.
2019/0009110 A1 1/2019 Gross et al.
2019/0009111 A1 1/2019 Myhr et al.
2019/0070069 A1 3/2019 Gertner et al.
2019/0076193 A1 3/2019 Clementi et al.
2019/0083161 A1 3/2019 Harle et al.
2019/0133642 A1 5/2019 Ignon et al.
2019/0143089 A1 5/2019 Ignon et al.
2019/0151637 A1 5/2019 Groop et al.
2019/0168016 A1 6/2019 Anderson et al.
2019/0183562 A1 6/2019 Widgerow
2019/0209859 A1 7/2019 Quisenberry et al.
2019/0224501 A1 7/2019 Burdette
2019/0239939 A1 8/2019 Boll et al.
2019/0240110 A1 8/2019 Sedic
2019/0240502 A1 8/2019 Anderson et al.
2019/0257320 A1 8/2019 Petit et al.
2019/0274759 A1 9/2019 Royon et al.
2019/0275320 A1 9/2019 Kim et al.
2019/0366067 A1 12/2019 Ginggen et al.
2020/0009007 A1 1/2020 Shadduck
2020/0016342 A1 1/2020 Ignon
2020/0030627 A1 1/2020 Eltorai et al.
2020/0093945 A1 3/2020 Jeong
2020/0101312 A1 4/2020 Pai et al.
2020/0114116 A1 4/2020 Dubey et al.
2020/0121354 A1 4/2020 Ginggen et al.
2020/0171289 A1 6/2020 Ignon et al.
2020/0179220 A1 6/2020 Jablow
2020/0206072 A1 7/2020 Capelli et al.
2020/0254273 A1 8/2020 Jafari et al.
2020/0275945 A1 9/2020 Knowlton
2020/0288843 A1 9/2020 Verheem
2020/0289161 A1 9/2020 Scooros
2020/0306555 A1 10/2020 Ebbesson
2020/0316270 A1 10/2020 Dijkstra et al.
2020/0330754 A1 10/2020 Kim et al.
2020/0338586 A1 10/2020 Park
2020/0367961 A1 11/2020 Podmore et al.
2020/0390468 A1 12/2020 Alexander
2021/0001148 A1 1/2021 Verheem
2021/0052292 A1 2/2021 Karni
2021/0085367 A1 3/2021 Shadduck et al.
2021/0128416 A1 5/2021 Danto
2021/0145479 A1 5/2021 Ignon et al.
2021/0154093 A1 5/2021 Boone, III et al.
2021/0154455 A1 5/2021 Ignon et al.
2021/0170150 A1 6/2021 Hong et al.
2021/0220631 A1 7/2021 Ok et al.
2021/0236342 A1 8/2021 Long et al.
2021/0236347 A1 8/2021 Carver
2021/0236836 A1 8/2021 Schwarz et al.
2021/0242657 A1 8/2021 Yi et al.
2021/0259914 A1 8/2021 Holbert
2021/0267625 A1 9/2021 Carver
2021/0268304 A1 9/2021 Lee
2021/0275406 A1 9/2021 Danto
2021/0282855 A1 9/2021 Boinagrov et al.
2021/0283421 A1 9/2021 Kang et al.
2021/0290430 A1 9/2021 Kim
2021/0330356 A1 10/2021 Del Rosario et al.
2021/0353922 A1 11/2021 Ignon et al.
2021/0361525 A1 11/2021 Park et al.
2021/0370049 A1 12/2021 Moss et al.
2021/0370089 A1 12/2021 Anash
2021/0393478 A1 12/2021 Bhatti
2021/0393974 A1 12/2021 Kim et al.
2021/0393975 A1 12/2021 Eltorai et al.
2021/0395071 A1 12/2021 Zubrum et al.
2021/0402208 A1 12/2021 Edgar
2022/0001198 A1 1/2022 Lee
2022/0001199 A1 1/2022 Beerwerth et al.
2022/0008122 A1 1/2022 Johnston et al.
2022/0032082 A1 2/2022 Shenfarber et al.
2022/0054189 A1 2/2022 Wootten
2022/0071491 A1 3/2022 Bae et al.
2022/0072332 A1 3/2022 Park et al.
2022/0087891 A1 3/2022 Goodman et al.
2022/0111198 A1 4/2022 Jung
2022/0117632 A1 4/2022 Walker et al.
2022/0125706 A1 4/2022 Horinek et al.
2022/0126014 A1 4/2022 Cederna et al.
2022/0133407 A1 5/2022 Anderson et al.
2022/0175443 A1 6/2022 Slatkine et al.
2022/0176092 A1 6/2022 Quan et al.
2022/0203112 A1 6/2022 Iger et al.
2022/0211424 A1 7/2022 Wootten et al.
2022/0218562 A1 7/2022 Capelli et al.
2022/0226668 A1 7/2022 Lee et al.
2022/0233400 A1 7/2022 Oh et al.
2022/0241107 A1 8/2022 Kim et al.
2022/0241146 A1 8/2022 Jeong
2022/0268536 A1 8/2022 Stephenson et al.
2022/0287910 A9 9/2022 Boone, III et al.
2022/0312940 A1 10/2022 Hong et al.
2022/0362529 A1 11/2022 Castro
2022/0401714 A1 12/2022 Quan et al.
2022/0409276 A1 12/2022 Choi
2023/0000523 A1 1/2023 Nicolas et al.
2023/0012684 A1 1/2023 Ignon et al.
2023/0014299 A1 1/2023 Lee, Jr. et al.
2023/0018295 A1 1/2023 Ignon et al.
2023/0019979 A1 1/2023 Deem et al.
2023/0033217 A1 2/2023 Ignon et al.
2023/0033761 A1 2/2023 Ignon et al.
2023/0042047 A1 2/2023 Kim et al.
2023/0055346 A1 2/2023 Fortkort et al.
2023/0062185 A1 3/2023 Nazarian et al.
2023/0104221 A1 4/2023 Aharon
2023/0123145 A1 4/2023 Ko
2024/0017046 A1 1/2024 Nebrigic et al.
2024/0033491 A1 2/2024 Ignon et al.
2024/0075263 A1 3/2024 Ignon et al.
2024/0139482 A1 5/2024 Ignon et al.

FOREIGN PATENT DOCUMENTS

CA 2340154 9/2002
CA 2784209 8/2011
CN 3292006 4/2003
CN 1708261 12/2005
CN 107920948 4/2018
CN 305941358 7/2020
CN 306109314 10/2020
CN 306995346 12/2021
CN 308188687 8/2023
DE 599521 7/1934
DE 2415633 10/1975
DE 3338057 8/1984
DE 3421390 12/1985
DE 234608 4/1986
DE 3503343 8/1986
DE 8330191 6/1987
DE 3740902 12/1988

(56) References Cited

FOREIGN PATENT DOCUMENTS

| | | | |
|---|---|---|---|
| DE | 4237940 | | 5/1993 |
| DE | 29808395 | | 8/1998 |
| DE | 10-2004-015815 | | 11/2005 |
| EM | Des. 8794184-0001 | | 12/2021 |
| EM | Des. 8880371-0001 | | 5/2022 |
| EM | Des. 015024621-0002 | | 6/2023 |
| EP | 0258901 | | 9/1987 |
| EP | 0479121 | | 4/1992 |
| EP | 0564392 | | 3/1993 |
| EP | 0784997 | | 7/1997 |
| EP | 1238643 | | 4/2000 |
| EP | 1453558 | | 9/2004 |
| EP | 2206483 | | 7/2010 |
| EP | 2544563 | | 9/2015 |
| EP | 2106780 | | 3/2016 |
| EP | 2865867 | | 5/2016 |
| EP | 3217899 | | 5/2016 |
| EP | 2240099 | | 2/2018 |
| EP | 2967633 | | 4/2018 |
| EP | 3302319 | | 4/2018 |
| EP | 3319573 | | 5/2018 |
| EP | 3340908 | | 7/2018 |
| EP | 2451367 | | 1/2020 |
| EP | 3388006 | | 3/2020 |
| EP | 2618797 | | 4/2020 |
| EP | 3237055 | | 8/2020 |
| EP | 3795204 | | 3/2021 |
| EP | 3437575 | | 4/2021 |
| ES | 1037776 | | 4/1998 |
| FR | 2712172 | | 5/1995 |
| FR | 2773461 | | 7/1999 |
| GB | 1372609 | | 10/1974 |
| GB | 2306351 | | 5/1997 |
| GB | 2585500 | | 1/2021 |
| GB | 6228949 | | 3/2022 |
| GB | 6228947 | | 9/2022 |
| IT | 553076 | | 12/1956 |
| IT | 1184922 | | 3/1985 |
| JP | 53-118927) | | 8/1963 |
| JP | S54-63580 | A | 5/1979 |
| JP | H05-042060 | | 2/1993 |
| JP | 1993-088552 | | 12/1993 |
| JP | 1997-294747 | | 11/1997 |
| JP | 2003-534881 | | 11/2003 |
| JP | 2003-339713 | | 12/2003 |
| JP | 2004-275721 | | 10/2004 |
| JP | 2006-503627 | | 2/2006 |
| JP | 2006-204767 | | 10/2006 |
| JP | 2012-527967 | | 11/2012 |
| JP | 2013-215621 | | 10/2013 |
| JP | D1581877 | | 7/2017 |
| JP | D1609357 | | 6/2018 |
| JP | 2018-527052 | | 9/2018 |
| JP | D1675782 | | 1/2021 |
| KR | 20-0280320 | | 7/2002 |
| KR | 10-20070070173 | | 7/2007 |
| KR | 10-2018-0030607 | | 3/2018 |
| KR | 10-1836310 | | 3/2018 |
| KR | 301238287.0000 | | 11/2023 |
| KR | 301238288.0000 | | 11/2023 |
| TW | D155201 | | 8/2013 |
| TW | D176752 | | 6/2016 |
| TW | D214226 | | 9/2021 |
| WO | WO 1994/024980 | | 11/1994 |
| WO | WO 1997/000707 | | 1/1997 |
| WO | WO 1997/011650 | | 3/1997 |
| WO | WO 1999/23951 | | 5/1999 |
| WO | WO 1999/37229 | | 7/1999 |
| WO | WO 2000/015300 | | 3/2000 |
| WO | WO 2000/79540 | | 12/2000 |
| WO | WO 2001/93931 | | 12/2001 |
| WO | WO 2004/108091 | | 12/2001 |
| WO | WO 2003/073917 | | 9/2003 |
| WO | WO 2004/037098 | | 5/2004 |
| WO | WO 2004/037287 | | 5/2004 |
| WO | WO 2005/061042 | | 7/2005 |
| WO | WO 2005/070313 | | 8/2005 |
| WO | WO 2006/018731 | | 2/2006 |
| WO | WO 2006/031413 | | 3/2006 |
| WO | WO 2007/114904 | | 10/2007 |
| WO | WO 2008/012324 | | 1/2008 |
| WO | WO 2009/086182 | | 7/2009 |
| WO | WO 2009/088884 | | 7/2009 |
| WO | WO 2009/097451 | | 8/2009 |
| WO | WO 2010/022396 | | 2/2010 |
| WO | WO 2010/068960 | | 6/2010 |
| WO | WO 2010/151704 | | 12/2010 |
| WO | WO 2011/006009 | | 1/2011 |
| WO | WO 2011/110840 | | 9/2011 |
| WO | WO 2012/131623 | | 10/2012 |
| WO | WO 2012/145667 | | 10/2012 |
| WO | WO 2013/030117 | | 3/2013 |
| WO | WO 2014/091035 | | 6/2014 |
| WO | WO 2014/151104 | | 9/2014 |
| WO | WO 2016/052818 | | 4/2016 |
| WO | WO 2016/106396 | | 6/2016 |
| WO | WO 2017/007939 | | 1/2017 |
| WO | WO 2017/111481 | | 6/2017 |
| WO | WO 2021/018765 | | 2/2021 |
| WO | WO 2021/113343 | | 6/2021 |
| WO | WO 2022/099318 | | 5/2022 |
| WO | WO 2023/039524 | | 3/2023 |
| WO | WO 2023/064718 | | 4/2023 |
| WO | WO 2023/164572 | | 8/2023 |

OTHER PUBLICATIONS

Amazon.com: leBilif Facial Skin Care Machine, posted Dec. 14, 2023 (retrieved online Mar. 29, 2024) from https://www.amazon.com/leBillif-Equipment-Esthetician-Essential-supplies/d (2023).
Amazon.com: Osaki LED Therapy Dome, posted date unavailable (retrieved online Mar. 29, 2024), from https://www.amazon.com/Osake-LED-Therapy-Dome/dp/BO8NN3BS7L (2024).
Beautimate adjustable Hydra Needle Microneedling Serium Applicator, https://www.beautimate.com/products/adjustable-hydra-needle, first accessed Aug. 12, 2023.
"BeautyBio: GLOfacial Hydro-Infusion deep pore cleansing + Blue LED clarifying tool", found online atamazon.com Sep. 26, 2023, ref. dated Nov. 15, 2022, retrieved https://www.amazon.com/GLOfacial-Hyrdo-Infusion-Deep-Cleansing-Clarifying/dp/BOBGJLMSZP/.
File History of Reissue U.S. Appl. No. 11/027,590, filed Dec. 29, 2004 (Reissue of U.S. Pat. No. 6,500,183, issued Dec. 31, 2002).
File History of Reexamination No. U.S. Appl. No. 90/007,683 (Reexamination of U.S. Pat. No. 6,241,739, issued Jun. 5, 2001).
File History of Reexamination No. 90/013,284, filed Jul. 2, 2014 (Reexamination of U.S. Pat. No. 6,241,739, issued Jun. 5, 2001).
Celluma Lite Compact LED Light Therapy Device fr Travel, posted date unavailable, (retrieved online Mar. 29, 2024), from https://www.celluma.com/products/celluma-lite (2024).
Cox III et al., Decreased Splatter in Dermabrasion, Arch Facial Plastic Surgery, Jan.-Mar. 2000, vol. 2, pp. 23-26.
Ditre et al., Effect of α-hydroxy acids on photoaged skin: A pilot clinical, histologic, and ultrastructuralstudy, Journal of American Academy of Dermatology, Feb. 1996, vol. 34, No. 2, Part 1, pp. 187-195.
Elipsa-Lightslim, posted date unavailable, (retrieved online Mar. 29, 2024), from https://www.lightslim.com/products/lightslim-elipsa (2024).
Harris et al., Combining Manual Dermasanding with Low Strength Trichloroacetic Acid to ImproveAntinically Injured Skin, The Journal of Dermatologic Surgery and Oncology, Jul. 1994, vol. 20, No. 7, pp. 436-442.
"Healthline: What is a HydraFacial and how does it work", found online at healthline.com Sep. 26, 2023, Ref. dated Dec. 9, 2020, https://www.healthline.com/health/what-is-hydrafacial.
Hydrafacial® Tower—User guide. Edge Systems. Revised Jun. 23, 2016. p. 16.

(56) References Cited

OTHER PUBLICATIONS

Hydrafacial Hydropeel Vortex Fusion Tips, https://mergesouq.com/products/hydrafacial-hydropeel-vortex-fusion-tips, first accessed Aug. 12, 2023.
HydraFacial MD Karma Spa Lounge & Beauty Bar, posted date unavailable (retrieved online Mar. 29, 2024), from https://www.karmabeautybar.com/hydrafacial-md (2024).
"InStyle: Why the HydraFacial is one of the most popular in-office treatments", found online atinstyle.com on Sep. 26, 2023, ref. dated Jun. 12, 2023, https://www.instyle.com/beauty/skin/hydrafacial-treatment-facts.
Microdermabrader Pepita Instruction Manual, Mattioli Engineering S.R.L., PEP_USA2.doc Rev 1.1, Sep. 29, 1997.
"Microderm Glo: Glo Mini", found online at microdermglo.com Sep. 26, 2023, ref. dated Sep. 27, 2019, https://www.microdermglo.com/collections/microdermabrasion-machines.
International Search Report and Written Opinion for PCT Application No. PCT/US2022/076203, mailed on Jan. 31, 2023, in 15 pages.
International Preliminary Report on Patentability and Written Opinion for PCT Application No. PCT/US2022/076203, dated Mar. 5, 2024, in 9 pages.

DEVICES, SYSTEMS AND METHODS FOR TREATING THE SKIN

CROSS-REFERENCE TO RELATED APPLICATIONS

This application claims the priority benefit of U.S. Provisional Patent Application No. 63/243,053, filed Sep. 10, 2021, the contents of which are incorporated by reference herein in their entirety.

BACKGROUND

Field

This application relates generally to skin treatment, and more specifically, to apparatuses, systems and methods for treating a person's skin.

Description of the Related Art

Abrasion of the outer layer or epidermis of the skin is desirable to smooth or blend scars, blemishes, or other skin conditions that may be caused by, for example, acne, sun exposure, and aging. Standard techniques used to abrade the skin have generally been separated into two fields referred to as dermabrasion and microdermabrasion. Both techniques remove portions of the epidermis called the stratum corneum, which the body interprets as a mild injury. The body then replaces the lost skin cells, resulting in a new outer layer of skin. Additionally, despite the mild edema and erythema associated with the procedures, the skin looks and feels smoother because of the new outer layer of skin.

SUMMARY

According to some embodiments, a skin treatment system comprises a main body portion, the main body portion comprising a receiving area configured to receive a treatment material container, the main body portion comprising a longitudinal axis, a waste container configured to be removably secured to the main body portion, a tip configured to be removably secured to the main body portion, the tip comprising a peripheral lip and at least one waste port, a pump, at least one fluid delivery conduit placing an interior of a treatment material container secured to the receiving area in fluid communication with the tip, and at least one waste conduit placing the at least one waste port of the tip in fluid communication with the pump, wherein activation of the pump creates a vacuum along the at least one waste conduit and the at least one waste port, wherein the pump is configured to transfer waste materials from the tip to the waste container via the at least one waste conduit, and wherein the pump is configured to contact waste materials being transferred to the waste container.

According to some embodiments, a skin treatment system comprises a main body portion, the main body portion comprising a receiving area configured to receive a treatment material container, the main body portion comprising a longitudinal axis, a waste container configured to be removably secured to the main body portion, a rechargeable battery, a base for receiving the main body portion, a tip configured to be removably secured to the main body portion, the tip comprising a peripheral lip and at least one waste port, a pump, at least one fluid delivery conduit placing an interior of a treatment material container secured to the receiving area in fluid communication with the tip, and at least one waste conduit placing the at least one waste port of the tip in fluid communication with the pump, wherein activation of the pump creates a vacuum along the at least one waste conduit and the at least one waste port, wherein the pump is configured to transfer waste materials from the tip to the waste container via the at least one waste conduit, wherein the pump is configured to contact waste materials being transferred to the waste container, and wherein the rechargeable battery is configured to be recharged when the main body portion is positioned within the base and the base is operatively coupled to an electric energy source.

According to some embodiments, the pump comprises a pump (e.g., liquid pump). In some embodiments, the pump does not comprise an air pump. In some embodiments, the pump comprises a metering or dosing pump. In some arrangements, the pump comprises a diaphragm pump. In some embodiments, the pump comprises one of the following pump types: a peristaltic pump, a piezoelectric pump, a gear pump, a piston pump, a syringe and another type of micro pump.

According to some embodiments, a skin treatment system comprises a main body portion, the main body portion comprising a receiving area configured to receive a treatment material container, the main body portion comprising a longitudinal axis, a waste container configured to be removably secured to the main body portion, a rechargeable battery positioned within an interior of the main body portion, a base for receiving the main body portion, a tip configured to be removably secured to the main body portion, the tip comprising a peripheral lip and at least one waste port, a pump (e.g., liquid pump), at least one fluid delivery conduit placing an interior of a treatment material container secured to the receiving area in fluid communication with the tip, and at least one waste conduit placing the at least one waste port of the tip in fluid communication with the pump, wherein activation of the pump creates a vacuum along the at least one waste conduit and the at least one waste port.

According to some embodiments, the pump is configured to transfer waste materials from the tip to the waste container via the at least one waste conduit, and wherein the rechargeable battery is configured to be recharged when the main body portion is positioned within the base and the base is operatively coupled to an electric energy source.

According to some embodiments, the pump (e.g., liquid pump) is configured to contact waste materials being transferred to the waste container. In some embodiments, the pump does not comprise an air pump. In some arrangements, the pump comprises a diaphragm pump. In other embodiments, the pump comprises one of the following pump types: a peristaltic pump (disc-based peristaltic diaphragm pump). a piezoelectric pump, a gear pump, a piston pump, a syringe and another type of micro pump.

According to some embodiments, non-liquid based pumps are included in the system (e.g., handpiece), either in lieu of or in additional to liquid pumps. In some embodiments, non-liquid pumps comprise air-based pumps (e.g., pumps that are configured that move air, either continuously or intermittently).

According to some embodiments, the system comprises a handheld device or handpiece configured for personal use by a subject undergoing a skin treatment procedure.

According to some embodiments, the system further comprises at least one controller (e.g., button, lever, switch, etc.) for regulating at least one operational aspect of the pump. In some arrangements, the at least one operational aspect of the pump comprises a flowrate of liquid passing through the pump and/or the pressure of liquid passing through the pump.

According to some embodiments, the tip comprises a rollerball, the rollerball positioned within an interior area defined by the peripheral lip and being configured to contact skin when the system is in use. In some embodiments, the rollerball comprises stainless steel. In some embodiments, the rollerball is solid throughout its cross section. In some arrangements, the rollerball extends distally past the peripheral lip of the tip.

According to some embodiments, the tip comprises at least one interior baffle to reduce a likelihood of short-circuiting fluid flow to the at least one waste port, wherein the at least one interior baffle is positioned within an area defined by the peripheral lip.

According to some embodiments, the tip is configured to abrade skin tissue as the system is moved relative to skin tissue of a subject. In some embodiments, the peripheral lip is configured to at least partially abrade skin tissue as the system is moved relative to skin tissue of a subject.

According to some embodiments, the pump (e.g., liquid pump) is configured to create suction along the tip when the longitudinal axis of the main body portion is maintained at an angle between 0 and 110 degrees relative to vertical.

According to some embodiments, the system further comprises at least one illumination source configured to provide light to the waste container. In some embodiments, the at least one illumination source comprises at least one light emitting diode (LED).

According to some embodiments, a suction created at the tip by the pump is 0 to 5 pounds per square inch (psi). In some embodiments, a maximum suction created at the tip by the pump is 5 pounds per square inch (psi).

According to some embodiments, the receiving area is configured to receive a disposable pod. In some embodiments, the receiving area comprises a piercing member configured to penetrate a portion of the treatment material container to place an interior of the treatment material container in fluid communication with the at least one fluid conduit.

According to some embodiments, the system comprises at least one automatic tag reader, wherein the tag reader is configured to obtain information from a tag positioned on a treatment material container positioned within the receiving area. In some embodiments, the at least one automatic tag reader comprises a RFID reader. In some arrangements, the at least one automatic tag reader is configured to both read and write to a tag.

According to some embodiments, the system further comprising a processor. In some embodiments, the processor is configured to operatively couple to a processor of an external device, system or network. In some arrangements, the device is configured to operatively couple to a smart device (e.g., smartphone, tablet, personal computer, etc.). In some embodiments, the device is configured to operatively couple to a cloud-based network or infrastructure.

According to some embodiments, the system further comprises at least one wireless network component configured to wirelessly communicate with an external device, system or network. In some embodiments, the at least one wireless network component comprises a short-range wireless technology (e.g., Bluetooth, Wi-Fi, Near-Field Communication (NFC), etc.)

According to some embodiments, the main body portion comprises an outer housing. In some embodiments, the outer housing comprises a that includes at least two components (e.g., that are configured to secure to each other to cover and protect the internal components of the system).

According to some embodiments, the outer housing is configured to withstand at least one environmental condition that the system is likely to encounter during use, such as, for example and without limitation, water or other liquid, low and/or high temperature, chemicals, and dropping or vibrations.

According to some embodiments, the tip and the receiving area are located along a same end of the system. In some embodiments, the tip and the receiving area are located along the top (or distal end) of the system.

According to some embodiments, the system generally comprises a figure “Y” when a treatment material container is positioned within the receiving area, wherein the tip and the treatment material container form a diverging upper portion of the figure “Y” and the main body portion with the waste container form a base portion of the figure “Y.”

According to some embodiments, the base is configured to be electrically coupled to an AC power source. In some embodiments, the base is configured to maintain the system in a substantially vertical orientation.

According to some embodiments, a method of treating skin comprises using a system according to any one of the system embodiments disclosed herein or equivalents thereof. In some embodiments, the method further comprises obtaining at least one separate treatment using a separate device. In some arrangements, the at least one separate treatment is administered by an aesthetician or another skin treatment professional. In some embodiments, the at least one separate treatment is not self-administered by a subject who is undergoing the skin treatment procedure. In some embodiments, separate treatments can be performed using a different type of skin treatment device or system than the one used by the subject (e.g., than the device or system used to perform self-administered treatment).

According to some embodiments, the method comprises multiple steps or phases. In some embodiments, the multiple steps or phases include at least two of the following: a cleansing step or phase, a hydrating step or phase and an abrasion step or phase. Further, the system can be configured to undergo a rinsing or cleaning step, phase or process. Such a cleaning or rinsing step can be performed between treatments and/or during a treatment, as desired or required.

According to some embodiments, a skin treatment system comprises a main body portion, the main body portion comprising a receiving area configured to removably receive a treatment material container, the main body portion comprising a longitudinal axis and the receiving area comprising a first offset axis, and a tip configured to be removably secured to the main body portion, the tip configured to contact skin tissue during use of the system, wherein the tip comprises a second offset axis, wherein the receiving area and the tip are positioned along the same end of the main body portion, and wherein the longitudinal axis of the main body portion, the first offset axis and the second offset axis for a “Y” shape.

According to some embodiments, the system is configured to generate a suction force along the tip. In some embodiments, the system is configured to generate a suction force along the tip using a pump (e.g., liquid pump). In some arrangements, the pump is configured to contact waste tissue transferred from the tip to a waste container. In one embodiment, the pump comprises a diaphragm pump.

According to some embodiments, the system comprises a handheld device or handpiece configured for personal use by a subject undergoing a skin treatment procedure. In some embodiments, the system additionally includes at least one controller for regulating at least one operational aspect of the pump. In some arrangements, the at least one operational aspect of the pump comprises a flowrate and/or pressure of liquid passing through the pump.

According to some embodiments, a skin treatment system comprises a working end configured to be placed in contact or proximate to contact with a skin surface being treated, and at least one transfer device configured to transfer a treatment material to or near the working end, wherein the at least one transfer device is configured to contact the treatment material.

According to some embodiments, the system comprises a waste container configured to receive spent treatment material and other debris removed from the working end. In some embodiments, the at least one transfer device comprises a pump (e.g., liquid pump). In some arrangements, the pump does not comprise an air pump. In some embodiments, the pump comprises a diaphragm pump. In some embodiments, the pump comprises one of the following pump types: a peristaltic pump, a piezoelectric pump, a gear pump, a piston pump, a syringe and another type of micro pump.

According to some embodiments, the system comprises a handheld device or handpiece configured for personal use by a subject undergoing a skin treatment procedure.

According to some embodiments, the skin treatment system further comprises at least one controller (e.g., buttons) for regulating at least one operational aspect of the at least one transfer device.

According to some embodiments, the at least one operational aspect comprises a flowrate and/or pressure of liquid passing through the pump.

According to some embodiments, the working end comprises a tip, wherein the tip comprises a rollerball, the rollerball positioned within an interior area defined by the peripheral lip and being configured to contact skin when the system is in use. In some embodiments, the rollerball extends distally past the peripheral lip of the tip.

According to some embodiments, the tip comprises at least one interior baffle to reduce a likelihood of short-circuiting fluid flow to the at least one waste port, wherein the at least one interior baffle is positioned within an area defined by the peripheral lip. In some embodiments, wherein the tip is configured to abrade skin tissue as the system is moved relative to skin tissue of a subject. In one arrangement, the peripheral lip is configured to at least partially abrade skin tissue as the system is moved relative to skin tissue of a subject.

According to some embodiments, the at least one transfer device is configured to create suction along the working end when a longitudinal axis of the system is maintained at an angle between 0 and 110 degrees relative to vertical.

According to some embodiments, the system further comprises at least one illumination source configured to provide light to the waste container. In some embodiments, the at least one illumination source comprises at least one light emitting diode (LED).

According to some embodiments, a suction created at the working end by the at least one transfer device is 0 to 5 pounds per square inch (psi). In some arrangements, a maximum suction created at the working end by the at least one transfer device is 5 pounds per square inch (psi).

According to some embodiments, a receiving area of the system is configured to receive a disposable pod, wherein the disposable pod is configured to contain the treatment material configured to be transferred to the working end. In some embodiments, the receiving area comprises a piercing member configured to penetrate a portion of a treatment material container to place an interior of the treatment material container in fluid communication with at least one fluid conduit of the system.

According to some embodiments, the system comprises at least one automatic tag reader, wherein the tag reader is configured to obtain information from a tag positioned on a treatment material container positioned in fluid communication with the system. In some arrangements, the at least one automatic tag reader comprises a RFID reader. In some arrangements, the at least one automatic tag reader is configured to both read and write to a tag.

According to some embodiments, the system further comprises a processor. In some arrangements, the processor is configured to operatively couple to a processor of an external device, system or network. In some embodiments, the device is configured to operatively couple to a smart device (e.g., smartphone, tablet, PC, other computing device, etc.). In some embodiments, the device is configured to operatively couple to a cloud-based network or infrastructure. In some arrangements, the system further comprises at least one wireless network component configured to wirelessly communicate with an external device, system or network (e.g., a short-range wireless technology, such as, for instance, Bluetooth, Wi-Fi, Near-Field Communication (NFC), etc.).

According to some embodiments, a method for treating skin comprises transferring a waste away from a working end of a skin treatment system, the skin treatment system having a main body portion, a tip and a waste canister, wherein the skin treatment system is configured to removably secure the tip and the waste canister to the main body portion, and wherein the skin treatment system comprises a at least one transfer device configured to transfer the waste away from the working end to the waste canister, the at least one transfer device being configured to contact the waste, and transferring a treatment material from a treatment material source to the working end.

According to some embodiments, the at least one transfer device comprises a pump. In some embodiments, the pump does not comprise an air pump. In some arrangements, the pump comprises a diaphragm pump. In some embodiments, the pump comprises one of the following pump types: a peristaltic pump, a piezoelectric pump, a gear pump, a piston pump, a syringe and another type of micro pump.

According to some embodiments, the system comprises a handheld device configured for personal use by a subject undergoing a skin treatment procedure. In some embodiments, the method further comprises regulating at least one operational aspect of the at least one transfer device. In one embodiment, the at least one operational aspect comprises a flowrate and/or pressure of liquid passing through the at least one transfer device.

According to some embodiments, the method further comprising illuminating the waste canister. In some embodiments, the method further comprises detecting at least one property of the waste contained in the waste canister.

According to some embodiments, a tip configured to be used in a skin treatment system comprise a rollerball, the rollerball positioned within an interior area defined by the peripheral lip and being configured to contact skin when the system is in use, wherein the rollerball extends distally past the peripheral lip of the tip, and wherein the tip comprises at least one interior baffle to reduce a likelihood of short-circuiting fluid flow to the at least one waste port, wherein the at least one interior baffle is positioned within an area defined by the peripheral lip. at least one portion configured to be placed at or near a skin surface being treated.

According to some embodiments, the container comprises a main portion, having at least one automatic tag receiving area, a neck portion comprising at least one member or area configured to be pierced to obtain access to an interior of the container, and at least one automatic identification tag positioned along the at least one automatic tag receiving area, wherein the at least one automatic identification tag is configured to include data and other information regarding contents of the container, and wherein the at least one automatic identification tag is configured to be automatically read once the container is positioned within a treatment system or device.

According to some embodiments, the main portion comprises a circular or substantially circular cross-sectional area. In some arrangements, the at least one member or area comprise a planar or substantially planar portion.

According to some embodiments, the at least one automatic identification tag comprises a RFID tag. In some embodiments, the at least one automatic tag is configured to be both read and written.

BRIEF DESCRIPTION OF THE DRAWINGS

These and other features, aspects and advantages of the present application are described with reference to drawings of certain embodiments, which are intended to illustrate, but not to limit, the present inventions. It is to be understood that these drawings are for the purpose of illustrating the various concepts disclosed herein and may not be to scale.

DETAILED DESCRIPTION

Although the various embodiments of a handpiece assembly have specific relevance to a skin treatment system, the features, advantages and other characteristics disclosed herein may have direct or indirect applicability in other applications, such as, for example, medical devices, mechanical devices and/or the like.

Several embodiments of the inventions disclosed herein are particularly advantageous because they include one, several or all of the following benefits and/or advantages: provide a device or system that can be used by the subject who is undergoing skin treatment for use by the actual subject being treated; provide a device or system that can be used by the subject who is undergoing skin treatment for use by the actual subject being treated between one or more treatments administered by a skin treatment professional (e.g., an aesthetician, a dermatologist, etc.) at a professional facility; provide enhanced delivery of treatment fluids to the skin of a subject; provide delivery of fluids to the skin of a subject while reducing the likelihood of contamination; provide enhanced collection of data regarding a skin treatment procedure; provide enhanced treatment protocols based on data collection and processing; and provide enhanced safety and other counterfeiting measures related to fluids delivered by skin treatment systems.

Figure 1:
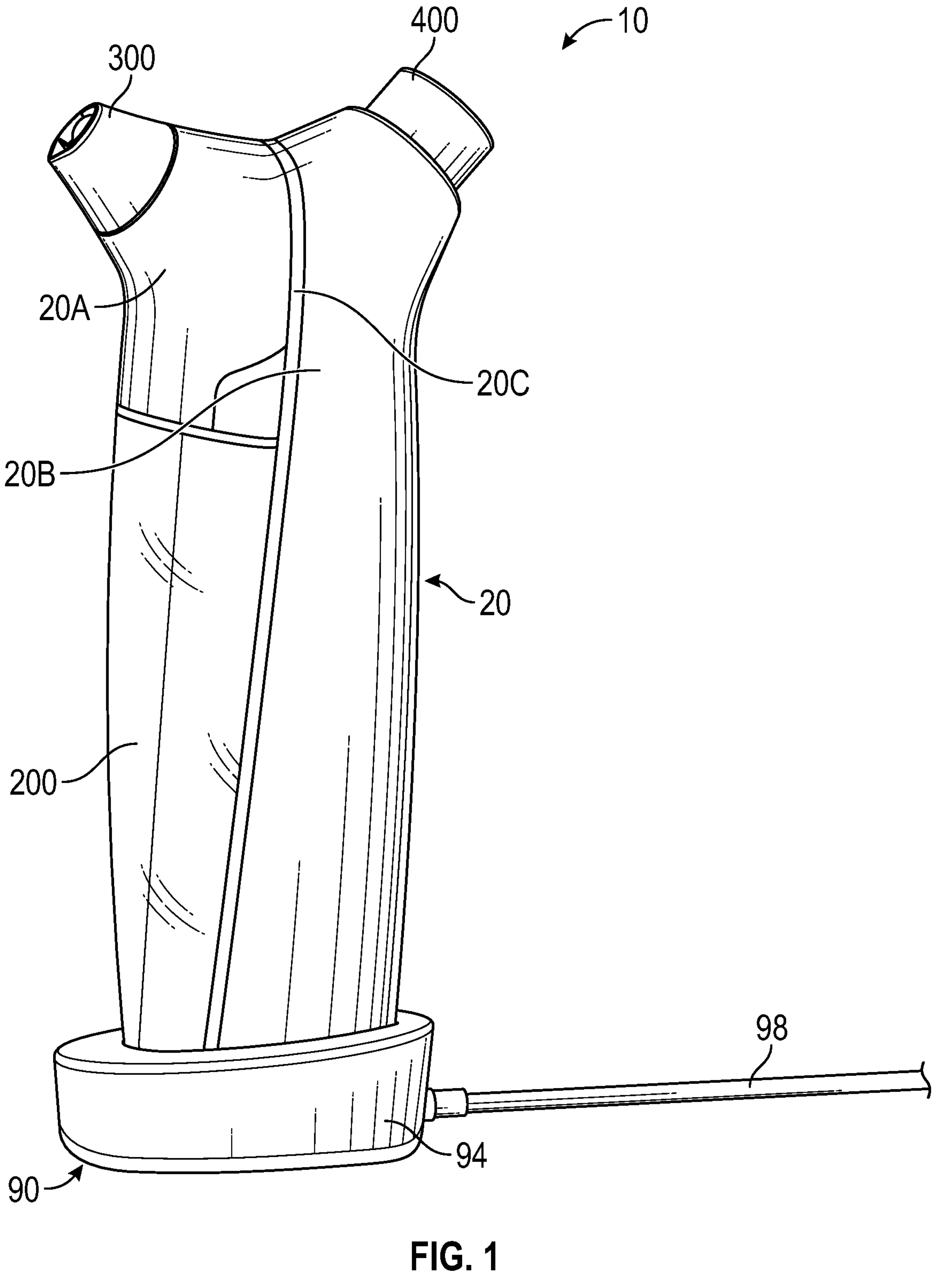
FIG. 1 illustrates a perspective view of a skin treatment system according to one embodiment.

FIG. 1 illustrates one embodiment of a skin treatment system 10. As noted herein, in some arrangements, the system 10 is configured to be used as a self-administered system by a subject undergoing skin treatment (e.g., dermabrasion or exfoliating procedure). However, in other embodiments, the system 10 may be used by someone other than the individual being treated (e.g., by an aesthetician, a dermatologist, another skincare professional, etc.) to perform a skin treatment procedure, as desired or required. In some embodiments, the system 10 is used to perform a procedure as a stand-alone treatment and/or as part of an overall treatment scheme (e.g., one that includes visits to an aesthetician or other professional).

In some embodiments, the system 10 can be used to perform one or more skin treatment procedures on a subject's skin by the subject itself. Such procedures or treatments can be performed between visits to a skin treatment professional and/or facility. For example, the various embodiments disclosed herein can be used to perform such intermediate treatments.

In some arrangements, self-administered or intermediate treatments are performed by the various embodiments disclosed herein, whereas professional treatments may be performed using a different device or system. However, in other arrangements, professional treatment can use the same device or system, as desired or required. In some embodiments, although the same system is used by both the subject and a skin treatment professional or other administrator of the procedure, the settings of the system can be modified.

For instance, the system can be used to provide a greater suction or vacuum when used by the professional or other r user.

With reference to FIG. 1, the system (e.g., the handpiece, the handheld device, etc.) 10 can include a main body portion 20. The main body portion 20 can comprise an outer housing that the user grasps and manipulates during operation of the system. In the illustrated arrangement, the main body portion 20 comprises an outer housing 20A, 20B that encloses and protects the internal components of the system. As illustrated, the housing can include two separate portions 20A, 20B that are configured to secure to one another along a connection interface 20C. In other arrangements, however, a system 10 can include a single or unitary housing and/or more than two portions (e.g., 3, 4, 5, more than 5, etc.) that are configured to secure to each other to form the outer housing, as desired or required. As illustrated in the embodiment of FIG. 1, the housing of the system can include a clamshell design.

The two or more portions 20A, 20B of a housing can be configured to be removably secured to each other via one or more releasable connections or methods. For instance, housing sections or portions 20A, 20B can be coupled to one another using one or more friction fit, press fit or snap fit connections. In other embodiments, glues or other adhesives, other mechanical fasteners (e.g., screws, rivets, flanges, tabs, other interlocking features, etc.) and/or any other securement method or technology can be used to couple two or more housing sections or portions of a system, as desired or required.

In alternative arrangements, the housing can include a single, monolithic structure. The housing can include a recess or opening into which one or more internal components may be inserted. By way of example, such a recess or opening can be located along the top or distal end of the system. In other embodiments, a recess or opening for a monolithically designed housing can be located along any other portion or area of the housing (e.g., the bottom or proximal end, a side, etc.), either in lieu of or in addition to an opening along the top or distal end. One or more caps or other sealing portions and/or another component of the system can be used to close any recesses or openings after the system is assembled and ready for use.

According to some embodiments, the housing and/or other external components of the system 10 comprise one or more thermoplastic materials that provide the desired or required resistance to elements that the system may be subjected, such as, for example, water or other liquids, chemicals or other substances, temperature variations, inadvertent dropping, vibration and/or other mechanical impact, etc.

In some configurations, at least a portion of the housing and/or other exterior areas of the main body portion 20 include surface texturing to facilitate with the handling of the system by a user. Such surface texturing can improve the overall feel and/or comfort of the system in the user's hand, reduce the likelihood of slippage and/or provide any other benefits or advantages. In some embodiments, such surface texturing can be included as a result of the manufacturing process in the component that will be exposed to the exterior of the system. Alternatively, such texturing can be applied after manufacture of the corresponding component(s) via the application of coatings or layers, roughening and/or the like. Thus, the texturing can be created while the housing components are being molded or otherwise formed or it can be created after formation of the components, as desired or required.

In some embodiments, the system is manufactured to be at least partially waterproof or water resistant. For instance, the system can be designed and otherwise manufactured to satisfy certain waterproofing standards. By way of example, the system can be configured to meet the requirements of IPxx, the ingress protection (IP) protection grade system drafted by IEC (International Electrotechnical Commission), which classifies electrical appliances according to their dust and moisture resistance. In some embodiments, the system complies with one or more IPxx standards (e.g., IP22).

As noted above, the system can be designed, manufactured and otherwise configured to meet certain standards with respect to drops, impacts, vibrations and the like. Further, in some embodiments, the system and/or its components (e.g., housing, internal components, etc.) are configured to include a temperature resistance of not only reasonably expected ambient conditions (e.g., 10 to 40 degrees C.), but also relatively extreme temperature conditions (e.g., −10 degrees C. to 50 degrees C. or higher). Further, the system can be configured to provide the necessary resistance to oils, chemicals and/or other materials to which a user may expose the system. For instance, the system 10 can be adapted to protect the housing and/or other system components against liquids and/or other fluids or materials used during the cleaning or sanitization and/or other maintenance of the system. According to some embodiments, the system is configured to sustain a drop from 1 meter or more (e.g., 1 m, 1.5 m, 2 m, 0 m to 1 m, 0 m to 2 m, 1.5 to 2 m, values between the foregoing ranges or values, etc.). In other arrangements, the system is configured to sustain a drop from greater than 2 meters (e.g., 2 m to 2.5 m, 2.5 m to 3 m, 2 m to 3 m, 2 m to 4 m, greater than 4 meters, distances between the foregoing values and ranges, etc.).

With continued attention to the embodiment illustrated in FIG. 1, the system 10 can include a waste container 200 that is configured to be removably secured to a side or area of the main body portion 20 (e.g., at least partially, to the housing). As shown, the waste container can be shaped, sized and otherwise configured to match the slopes, contours, lines and/or other exterior features of the adjacent components (e.g., the main body portion 20) of the system. As a result, the system 10 can include a smooth and seamless overall shape. Such a configuration can enhance the feel to the user and/or the look of the system. According to some embodiments, waste container and/or other portions of the system comprise, without limitation, one or more of the following materials: acrylonitrile butadiene styrene (ABS), polycarbonate (PC), polypropylene (PP), thermoplastic elastomers (TPE) and/or the like. However, in other arrangements, one or more components and/or portions of the system include other materials (e.g., other thermoplastic materials, metals or alloys, glass, other natural or synthetic materials, etc.), either in lieu of or in addition to the specific thermoplastic materials listed herein.

In some embodiments, some or all portions of the waste container 200 that are exposed to the exterior of the system 10 are at least partially transparent or translucent to permit a user to view inside the waste container 200 (e.g., during use of the system, between procedures, etc.). The waste container 200 can comprise one or more thermoplastic materials that are transparent or translucent, as desired or required. In the depicted arrangement, the entire waste container 200 or substantially the entire waste container 200 is transparent or translucent. However, in alternative configurations, only a portion of the waste container is transparent or translucent. For example, the waste container can include a window or other area that is transparent or translucent, while the remainder of the waste container is not transparent or translucent (e.g., is opaque, solid, etc.). The area of the window or other viewable portion can be 5% to 40% (e.g., 5 to 40, 10 to 40, 10 to 30, 10 to 20, 5 to 25, 10 to 20%, percentages between the foregoing values or ranges, etc.) of the overall exterior surface area of the system. In other embodiments, the area or size of the window or viewable portion is less than 5% or greater than 40% of the overall exterior surface area of the system. In other embodiments, the waste container does not include any transparent, translucent and/or other viewable portions.

As discussed in greater detail below, the system 10 can include one or more illumination sources (e.g., LED) that provide light to the interior of the waste container 200. Such illumination can serve one or more purposes and/or provide one or more benefits or advantages to the system and the user. For instance, illumination of the waste container can facilitate in assessing or otherwise evaluating (e.g., qualitatively, quantitatively, comparatively, etc.) the effectiveness of a skin treatment procedure. In some embodiments, the turbidity or cloudiness of the spend fluid and other waste collected within the waste container 200 can provide certain insight to a user regarding how well a treatment procedure (or a step or portion of a procedure) was performed and/or regarding some other aspect of a procedure itself and/or the person who is undergoing the procedure (e.g., how much dirt, sebum and/or other materials were removed from the subject, the effectiveness in removing certain types of materials, etc.).

In some embodiments, the system can include one or more sensors to help analyze and quantitatively assess the contents of the waste container 200. For example, the system 10 can include a turbidity sensor or similar sensor adjacent one or more portions of the waste container 200. Such sensors can be built into the system and/or can be external to the system, as desired or required. In some embodiments, such sensors are light-based sensors that determine how cloudy or clear the contents collected in the waste container are. In other arrangements, other types of sensors can be used, such as, for example, pH sensors, temperature sensors, sensors that are configured to detect or at least approximate the presence of certain components (e.g., salts, oils, etc.) and/or the like.

Figure 9A:
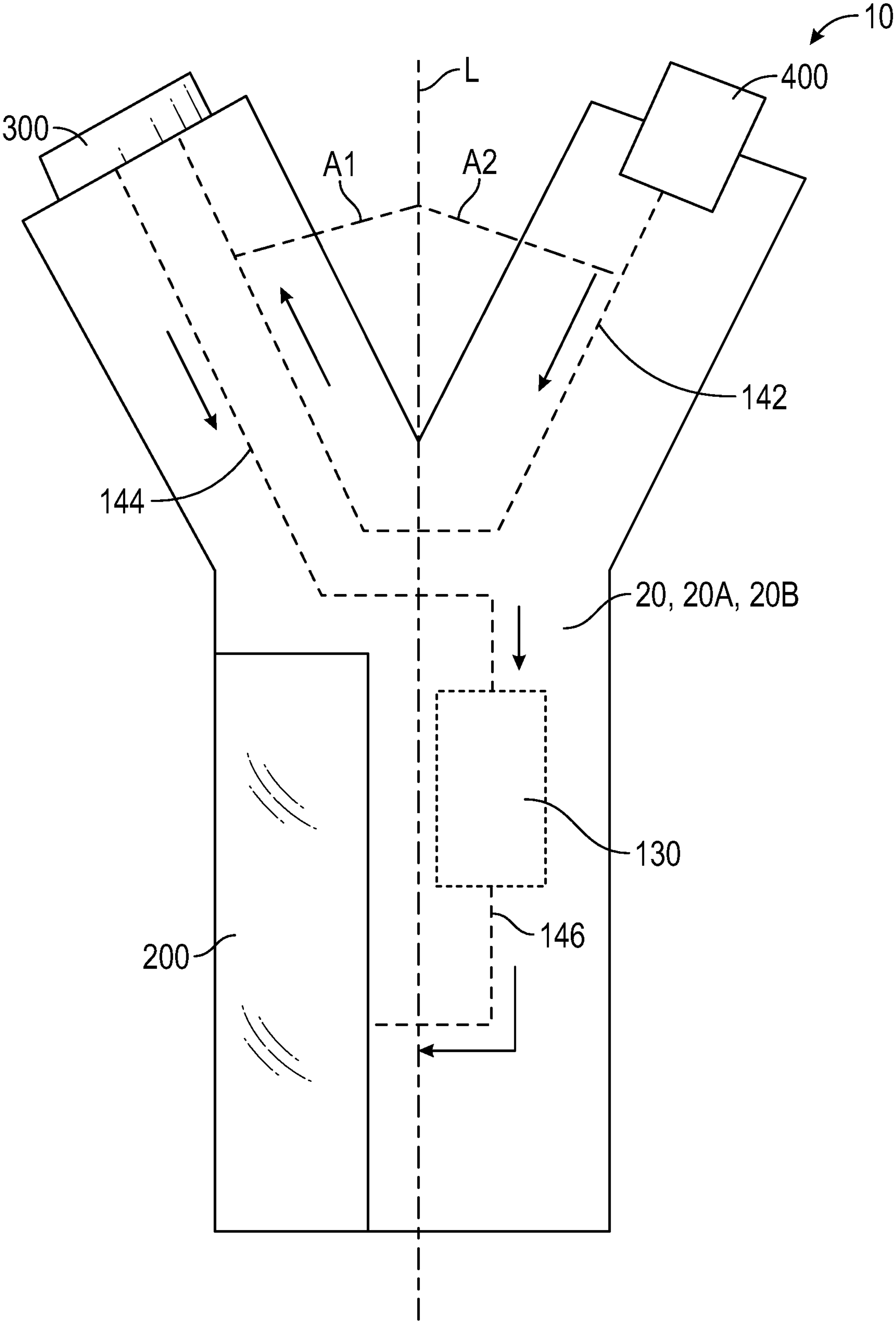
FIG. 9A schematically illustrates a skin treatment system according to one embodiment.

With continued reference to FIG. 1, the system 10 can additionally include a tip 300 located along the top or distal end of the system 10. In some arrangements, as depicted in FIG. 1, the tip 300 is angled relative to a vertical or longitudinal axis of the system. As illustrated in FIG. 9A, such an angle A1 between the vertical or longitudinal axis L of the device and the tip 300 can be 5 to 50 degrees (e.g., 5 to 50, 5 to 25, 25 to 50, 10 to 40, 10 to 30, 15 to 30, 20 to 30, 20 to 45, 15 to 45 degrees, angles between the foregoing angles and ranges, etc.). In other arrangements, the angle A1 can be less than 5 degrees or greater than 50 degrees, as desired or required. The angled design of the distal end of the tip 300 can facilitate the user (e.g., the subject undergoing a self-administered treatment procedure, an aesthetician or other professional performing a procedure on a subject, etc.) during the execution of a treatment procedure. An angled distal end of the tip 300 can effectively increase the surface area of the portion of the tip that actually contacts the skin surface being treated, enhance the ability of the user to maintain contact with the targeted skin surface, improve the comfort and ergonomic features for the user and/or provide one or more additional advantages or benefits, as desired or required.

As shown in FIG. 1, the tip 300 can be sized, shaped and otherwise configured to maintain a smooth or substantially smooth outer shape of the system 10. In other words, the exterior lines and overall shape of the system 10 can be generally smooth with continuous (e.g., uninterrupted) contours or lines. Additional details regarding the tip 300 are provided below.

The system 10 can be configured to receive a pod, vial or other container 400. In some embodiments, such a pod 400 contains one or more treatment serums, other liquids and/or other treatment materials. The contents of the pod 400, once the pod 400 has been secured to the system 10, can be placed in fluid communication with one or more portions (e.g., fluid conduits or passages, other internal portions or components of the system, etc.) to selectively transfer the contents from the pod to the tip (e.g., by activating a fluid pump or otherwise generating a vacuum or suction force along the tip).

As is the case with the tip 300 in the illustrated embodiment, once secured to the system 10, the pod or other container 400 can be angled relative to a vertical or longitudinal axis of the system. With reference to FIG. 9A, such an angle A2 between the vertical or longitudinal axis L of the device and the longitudinal axis of the pod or other container 400 (and thus, the longitudinal axis of the receiving area of the system that receives the pod or container) can be 5 to 50 degrees (e.g., 5 to 50, 5 to 25, 25 to 50, 10 to 40, 15 to 45 degrees, angles between the foregoing angles and ranges, etc.). In other arrangements, the angle A2 can be less than 5 degrees or greater than 50 degrees, as desired or required. Therefore, in some arrangements, both tip 300 and the pod or container 400 (once secured to the system) are angled relative to the longitudinal axis of the system and/or to one another, as desired or required. In some embodiments, the overall shape of the system forms a "Y." This becomes more evident when a pod or other container 400 and a tip 300 are secured to the system (e.g., handpiece, handheld device) 10. See, for example, FIGS. 1 to 3B, 7A, 7B, 9A and 9B. Thus, in some embodiments, the system 10 comprises a "Y" shape with the upper portion of the "Y" formed by the tip and the container, and the lower portion of the "Y" formed by the main body portion (which may include a waste container).

As discussed in greater detail below, the system 10 can include a battery (e.g., an internal rechargeable battery) to selectively energize the various electrical components of the system (e.g., fluid pump, lights, sensors, processors, etc.). Accordingly, in some embodiments, as depicted in FIG. 1, the main body portion 20 is sized, shaped and otherwise adapted to fit within a docking station 90 and/or vice versa. The docking station 90 can include a recess or opening located in a base 94 for receiving the main body portion (e.g., the bottom of the main body portion). In some arrangements, the docking station is configured to securely maintain the main body portion, and thus the system, in an upright or vertical orientation when the main body portion is placed therein and secured thereto.

With continued reference to FIG. 1, the docking station 90 can include a base 94 (e.g., into which the main body portion 20 is configured to be positioned). As shown, a cable or other electrical connector 98 can electrically couple the base 94 to an electrical energy source (e.g., AC power). In other embodiments, the system is configured to receive one or more batteries (e.g., individual battery (ies), battery packs, etc.) that can be replaceably removed from the system for recharging (e.g., using a separate charger or other charging device), replacement, etc., as desired or required.

Figure 2A:
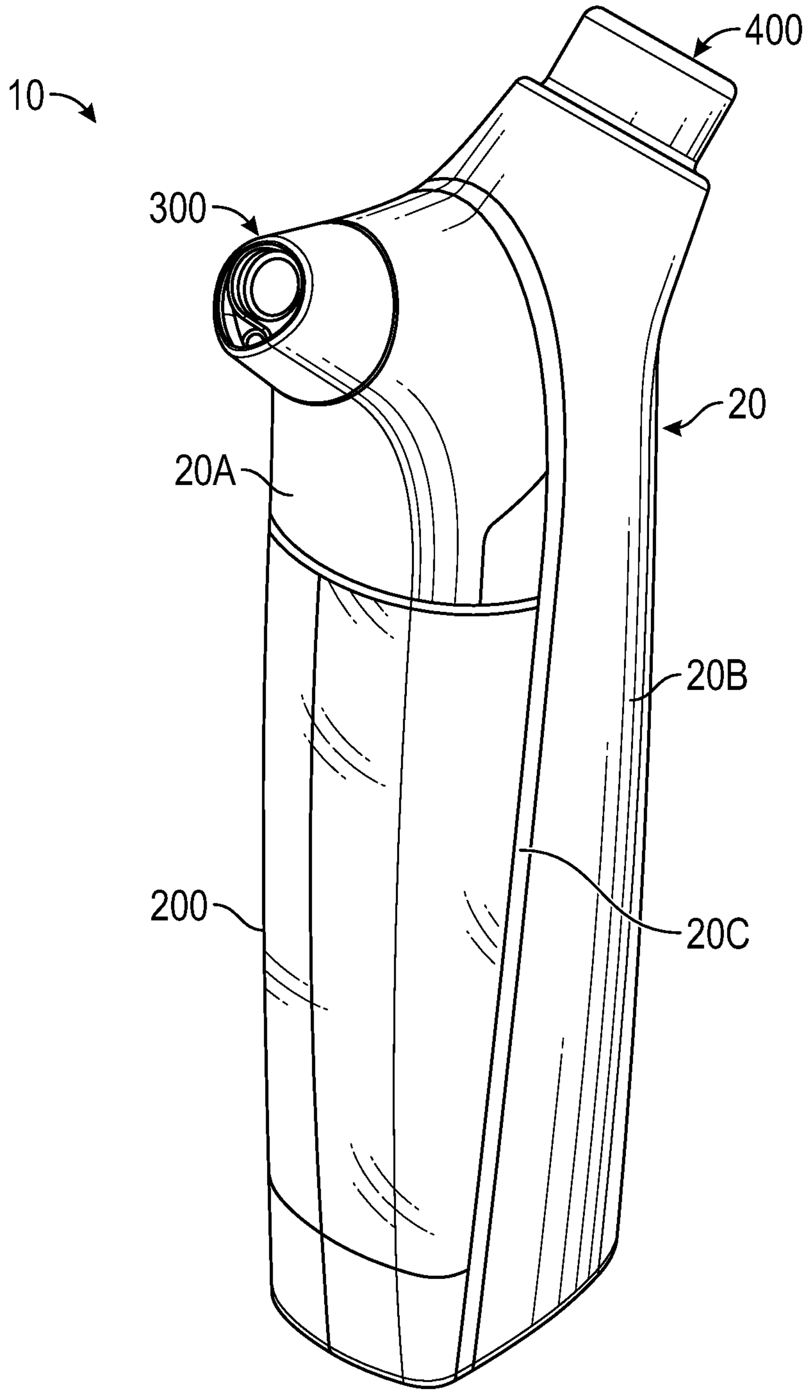
FIGS. 2A and 2B illustrate different perspective views of the skin treatment system of FIG. 1.
Figure 2B:
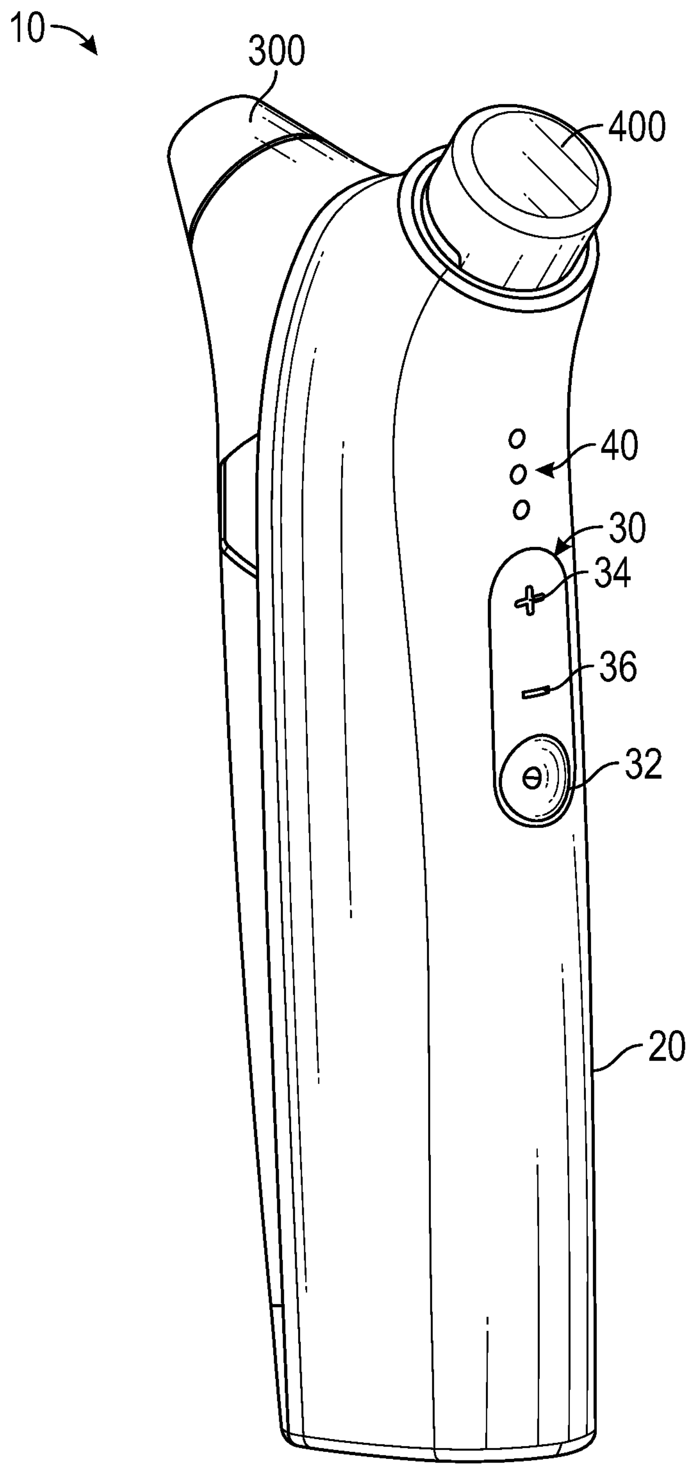

FIGS. 2A and 2B illustrate different perspective views of the skin treatment system 10 of FIG. 1. As illustrated in FIG. 2B, the system (e.g., handpiece, handheld device, etc.) 10 can include one or more controllers 30 along its exterior surface (e.g., along the outer housing of the main body portion 20). In the depicted embodiment, the system 10 comprises an ON/OFF button 32 and "plus" and "minus" buttons 34, 36 to control the pressure, flowrate and/or other properties associated with a liquid pump situated within the system. In other embodiments, the controllers include switches, dials, a touchscreen (e.g., on the device and/or a separate device that is operatively coupled to the device, etc.). Additional information regarding the liquid pump and other internal components of the system are provided below.

In some embodiments, the buttons or other controllers 30, 32, 34, 36 are positioned such that a user can easily press or otherwise manipulate the controllers while grasping and using the system 10 (e.g., using a single hand to both grasp the device/system and make changes to an operational parameter of the device/system using one or more controllers). For example, the position, orientation, configuration and/or other details regarding the controllers can advantageously permit a user to adjust the controllers using a single hand while performing a skin treatment procedure (e.g., while still grasping and manipulating the system). In other embodiments, however, the operation and/or control of the system 10 can be performed differently (e.g., without the use of buttons or other controllers incorporated into the main body portion 20 or other surface of the system), as desired or required. For instance, the system 10 can be configured to be operatively coupled (e.g., using one or more wireless or wired connections) to a separate computing device, such as, a smartphone, a tablet, a personal computer, etc. In such configurations, the separate computing device can be adapted to allow a user to make the necessary adjustments via a user interface (e.g., an application, program, etc.).

With further reference to FIG. 2B, the system 10 can also include one or more indicators or other output 40. For example, the system 10 can comprise one or more status lights, displays and/or the like that provide information to the user. In some embodiments, the outputs 40 are light emitting diodes (LEDs) that are configured to inform the user of certain conditions or occurrences, such as, for instance, whether the system is powered on, the current pressure/vacuum level of the internal fluid pump, the flowrate of the fluid being transferred from the pod or other container secured to the system to the tip, the battery life of the battery or other power source of the system, the system temperature, elapsed time or remaining time for a procedure and/or the like. As noted herein, the system 10 can be operatively coupled (e.g., wirelessly, using a wired connection, etc.) to a separate computing device (e.g., smartphone, tablet, personal computer, network, cloud or similar infrastructure, etc.) that can display such information to the user, either in lieu of or in addition to any indicators or outputs 40 positioned on the system (e.g., the main body portion 20) itself.

In some embodiments, one or more of the controllers and/or the indicators associated with a specific device or system are provided on a separate device, component and/or system. For instance, such a separate device can include, without limitation, a smartphone, a tablet, a main or system component to which the system can operatively couple (e.g., a tower or console, a main processing unit, etc.), another computer device (e.g., a personal computer, a network, a cloud infrastructure, etc.), a separate input/output device, etc., as desired or required.

Figure 3A:
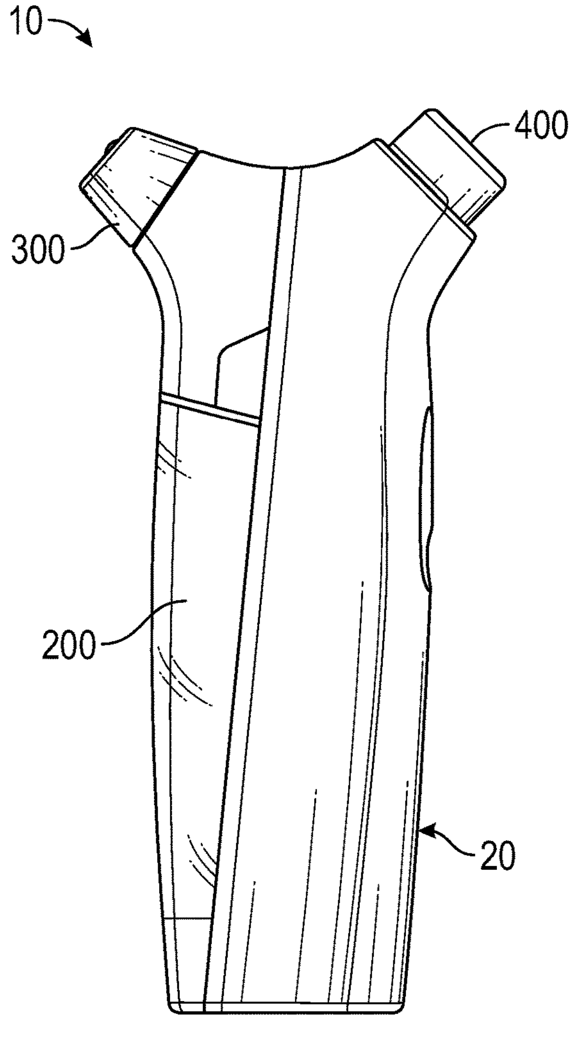
FIGS. 3A and 3B illustrate different side views of the skin treatment system of FIG. 1.
Figure 3B:
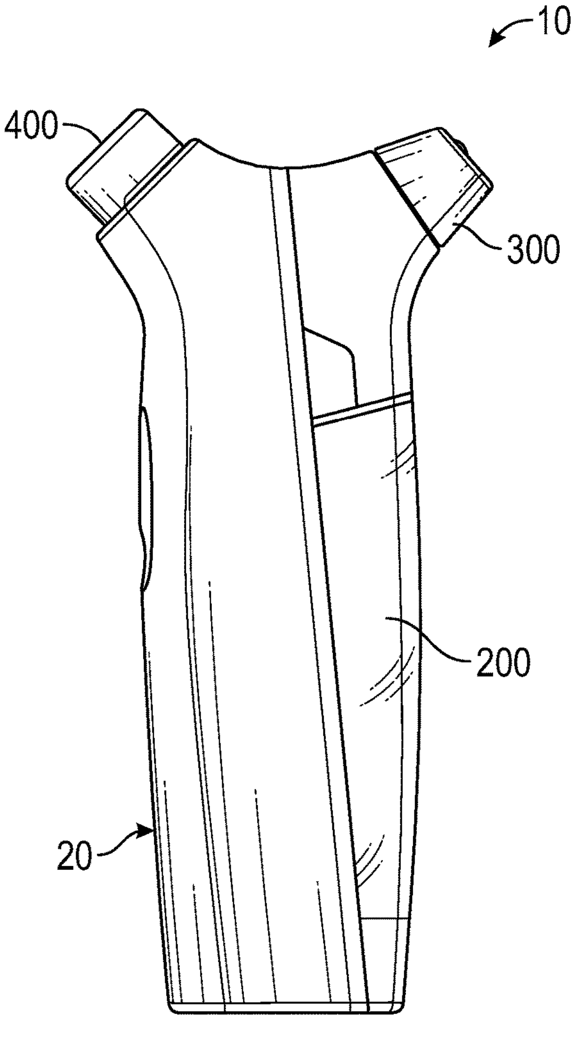
Figure 4A:
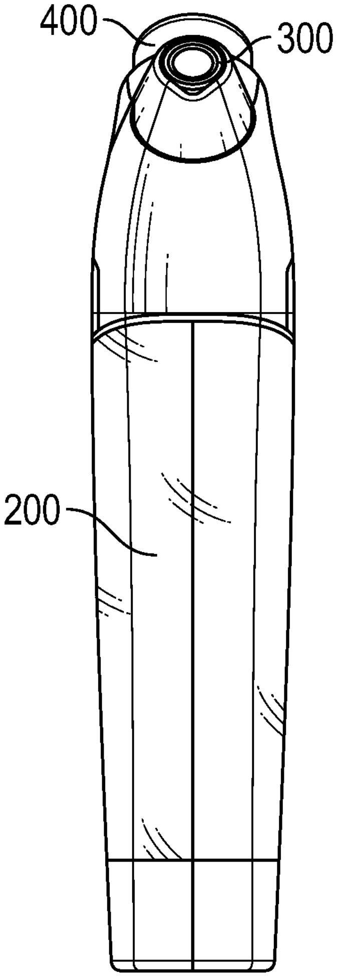
FIGS. 4A and 4B illustrate front and rear views of the skin treatment system of FIG. 1.
Figure 4B:
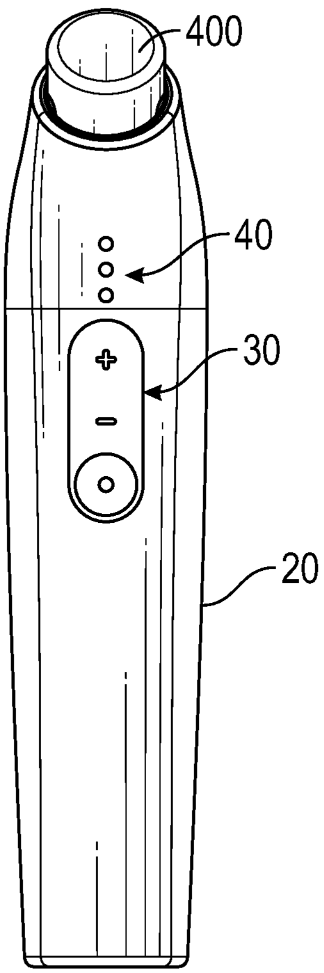
Figure 6:
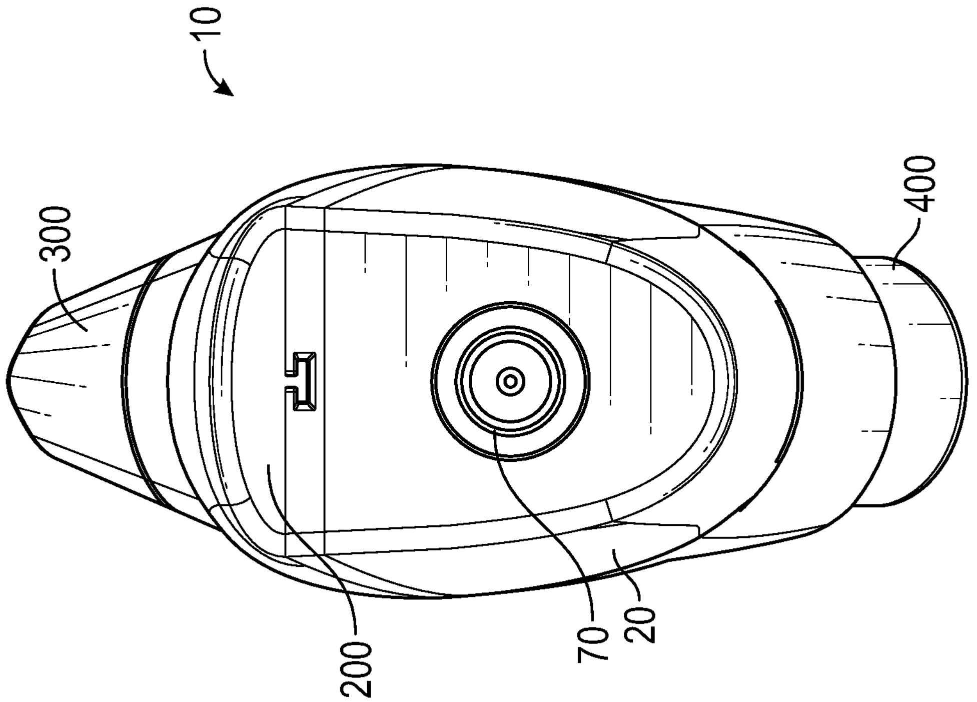
FIGS. 5 and 6 illustrate top and bottom views of the skin treatment system of FIG. 1.
Figure 5:
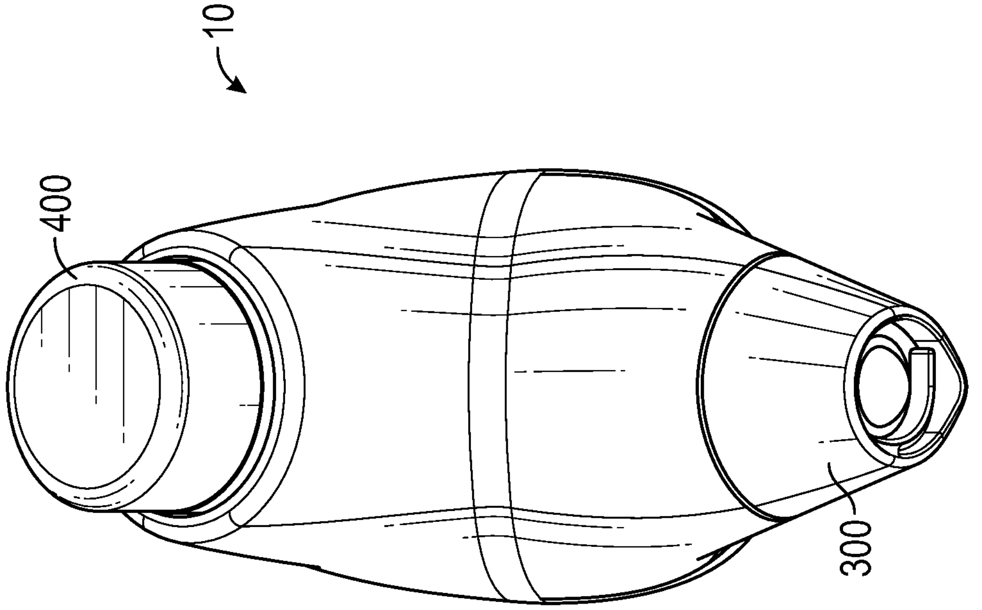

FIGS. 3A and 3B illustrate different side views of the system 10 of FIG. 1. Likewise, FIGS. 4A and 4B illustrate front and rear views of the system 10 of FIG. 1. Further, FIG. 5 illustrates a top view of the system 10 of FIG. 1. As illustrated in the bottom view of the system 10 in FIG. 6, the system 10 can include an electrical pad or other electrical contact area 70 along or near the bottom end. Such an electrical pad or contact area 70 can be sized, shaped, positioned and otherwise configured to contact a corresponding electrical contact area (not shown) of the charging/docking station 90. Thus, the battery (ies), battery pack, other rechargeable power source, etc. included in the system (e.g., handpiece) 10 can be advantageously charged once the main body portion is docked. In other embodiments, such electrical pads or contact areas can be positioned along different portions of the system and/or the docking station 90, as desired or required. In some arrangements, the battery or batteries of the system 10 can be charged using a hardwired connection that plugs into the main body portion or other section or component of the system 10, using inductive charging technology and/or the like. In yet other embodiments, the system 10 can be adapted to receive disposable or non-rechargeable batteries.

Figure 7A:
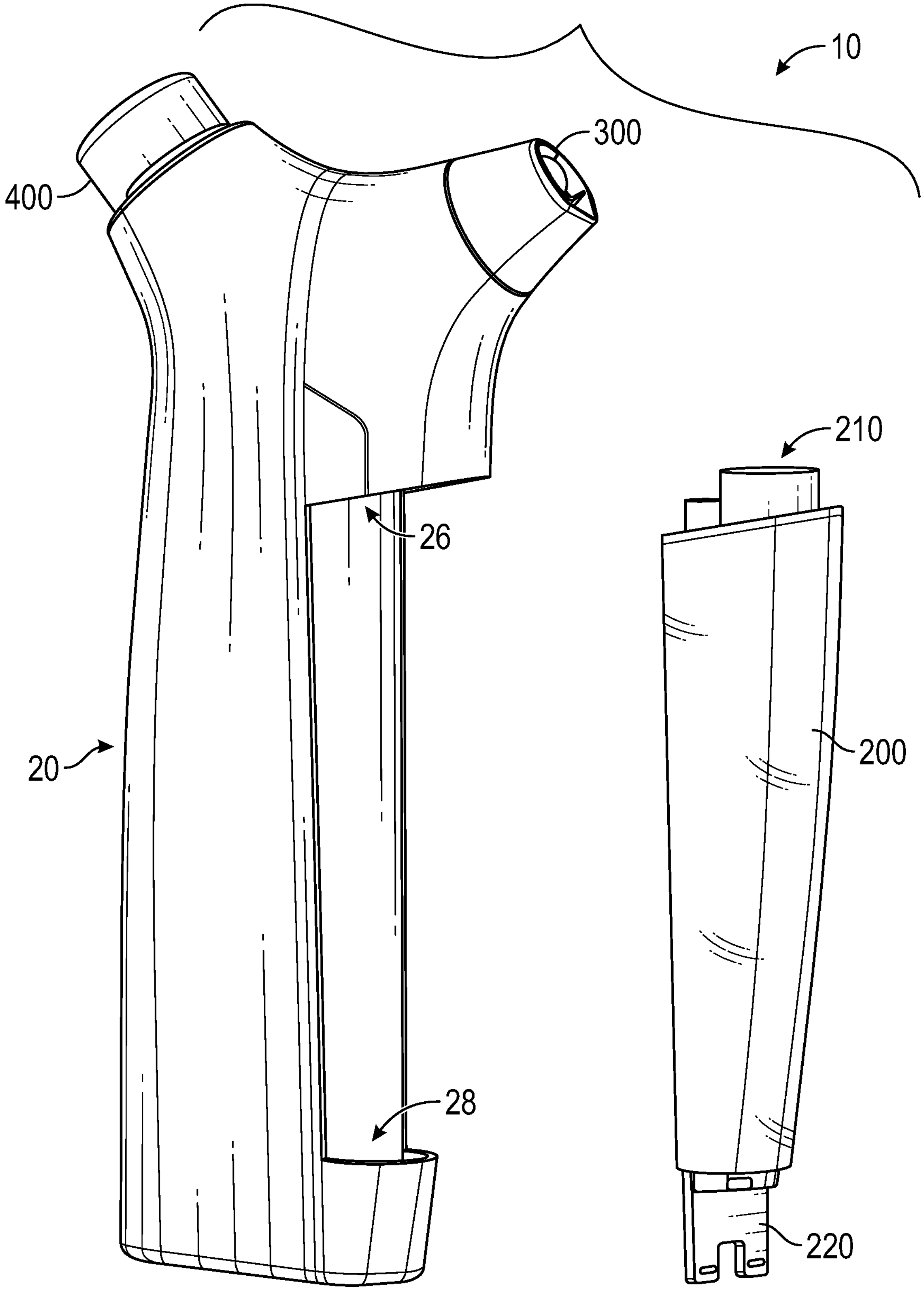
FIG. 7A illustrates an exploded perspective view of the skin treatment system of FIG. 1 with the waste canister separated from the main body portion.

FIG. 7A illustrates a partially exploded perspective view of the treatment system (e.g., handpiece, handheld device, etc.) 10 of FIG. 1 with the waste canister 200 separated from the main body portion 20. As shown, the main body portion 20 can include upper and lower recesses or openings 26, 28 that are shaped, sized and otherwise configured to receive corresponding portions (e.g., tabs, extensions, etc.) 210, 220 of the waste container 200. In some embodiments, for example, a lower tab or extension 220 of the waste container 200 can include a reflector portion that is configured to be placed adjacent one or more LEDs (and/or other light emitting device or sources) of the main body portion 20 once the waste container 200 has been properly secured to the main body portion. Such a reflector portion can help at least partially disperse and/or distribute the light from the LEDs or other light source to create a desired illumination effect within, around and/or the vicinity of the waste container 200. Further, the upper portion 210 of the waste container 200 can include the necessary hydraulic and/or other fluidic connections and/or components to facilitate the delivery of waste materials (e.g., spent fluid, removed tissue, other waste, etc.) into the interior of the waste canister or container 200, as desired or required. In some embodiments, the waste container or canister 200 is configured to reversibly lock relative to the main body portion 20 of the system 10 to ensure that waste materials are predictably delivered into the waste container 200. In some embodiments, the container includes an air bleed opening or other venting feature (e.g., to facilitate with transfer of fluids to the container). Further the container can include one or more markings, such as, for example, volume graduation marks, a maximum fill line and/or the like.

Figure 7B:
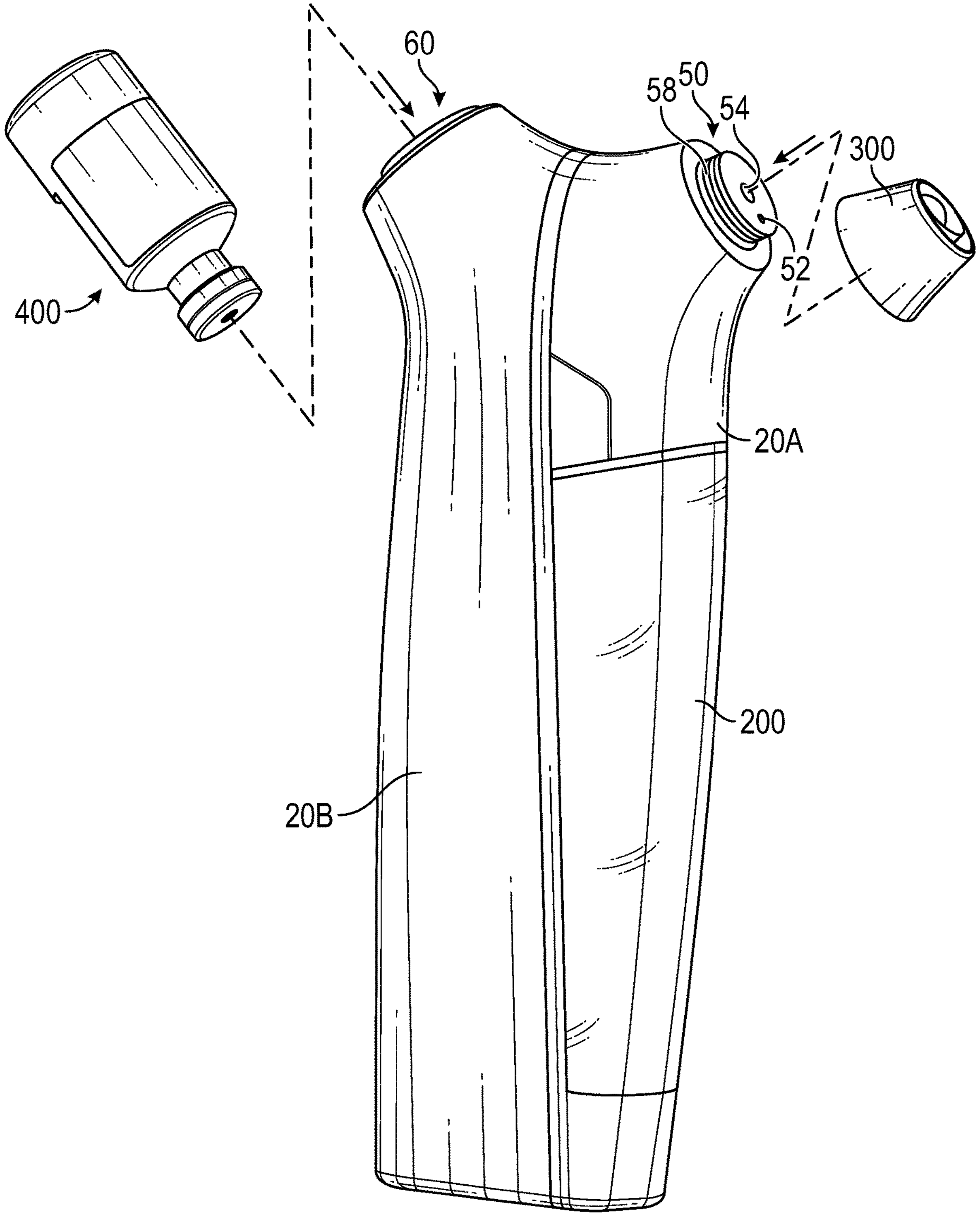
FIG. 7B illustrates an exploded perspective view of the skin treatment system of FIG. 1 with the tip and the treatment material container or pod separated from the main body portion.

FIG. 7B illustrates a different exploded perspective view of the skin treatment system 10 of FIG. 1 with the waste canister or container 200 secured to the main body portion 20, but the tip 300 and a pod or other treatment material container 400 separated from the main body portion 20. As shown by the arrows in FIG. 7B, the tip 300 can be secured to a corresponding tip-receiving area 50 of the main body portion 20, and the pod or other container 400 can be secured to a corresponding receiving area 60.

In some embodiments, the system can be activated and used (e.g., to perform a desired skin treatment procedure) once the tip and container (e.g., pod) have been secured to the housing or main body portion 20 of the system. In some arrangements, the system will not be permitted to be electrically activated (e.g., to turn on) unless both the tip and a container are appropriately secured to the system. In some embodiments, the system includes sensors (e.g., RFID or other identification tag readers) that help ensure that appropriate tip and/or container (e.g., pod) have been secured to the system. In some arrangements, the system can be configured to turn on only when acceptable tips and/or containers have been secured to the corresponding portions of the system. This can help improve efficacy and safety of a skin treatment procedure being performed using any of the embodiments of the system disclosed herein or equivalents thereof.

With continued reference to FIG. 7B, the tip-receiving area 50 can include a protruding portion (e.g., a circular protruding portion) that is shaped, sized and otherwise configured to receive a removable (e.g., disposable) tip 300. The tip-receiving area 50 can include one or more fluid delivery ports or openings 54 and one or more waste ports or openings 52. Such ports or openings 52, 54 can be positioned, sized, shaped and/or otherwise adapted to align (e.g., or substantially align) and be placed in fluid communication with corresponding fluid passages and/or ports of the tip 300. Further, one or more O-rings and/or other sealing members 58 can be used at or near the tip/tip-receiving area interface to prevent or reduce the likelihood of leaks of treatment fluid/materials and/or waste materials between transferred to and/or from the tip 300 during operation of the system.

Figure 9B:
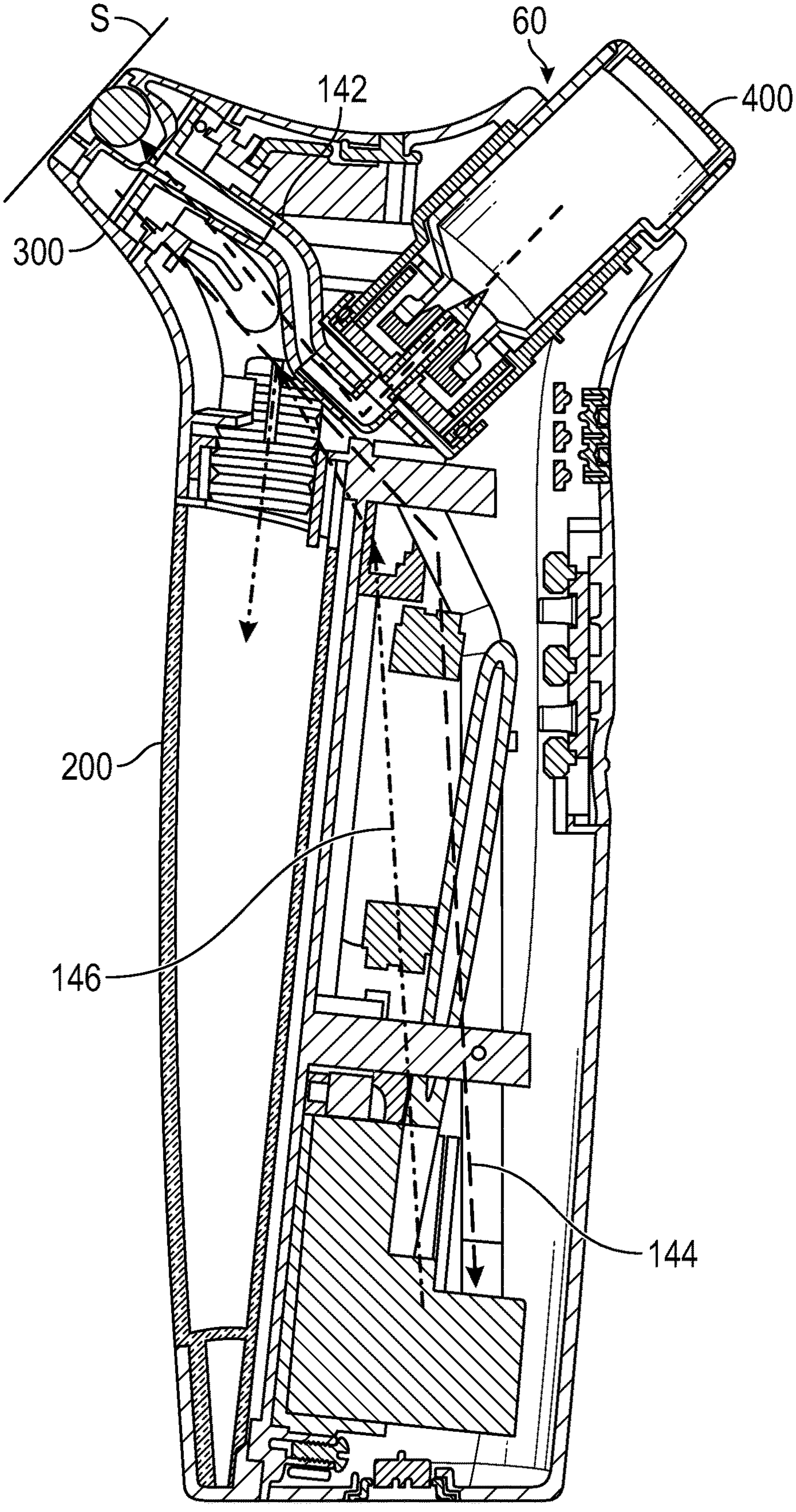
FIG. 9B illustrates a cross-sectional view of the skin treatment system of FIG. 1.

As depicted in the cross-sectional view of FIG. 9B, the receiving area 60 of the main body portion 20 can include a spike or other piercing or penetrating member or feature 62 that is configured to penetrate or otherwise undermine a septum, membrane or other portion of the pod or container 400 that is positioned within the receiving area. Such a piercing member 62 can be cannulated to access the interior of the pod 400 and to provide a fluid pathway from the interior of the pod to one or more conduits or other fluid passages of the system once the pod is secured to the system (e.g., within the receiving area). Accordingly, pods or other treatment material containers 400 configured for use with the system 10 can comprise a membrane, septum and/or other penetrable portion or member to access its interior portion and contents. Such membranes or other members can include one or more flexible, semi-rigid and/or rigid materials and/or construction, such as, for example, thermoplastic materials, rubber, metal or alloys (e.g., aluminum) and/or the like. Additional details regarding pods and other containers 400 for use with the system 10 are provided below.

Figure 8:
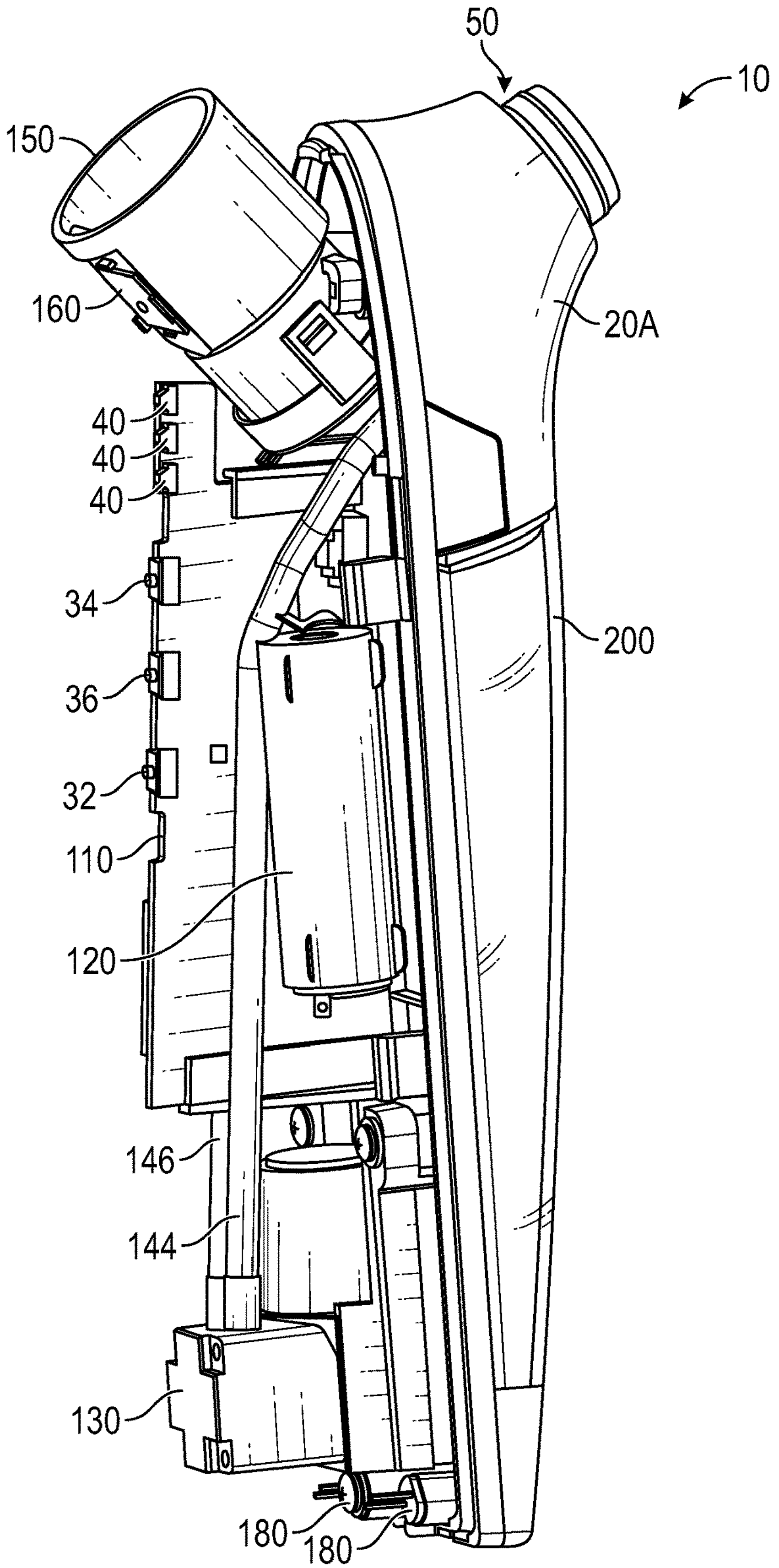
FIG. 8 illustrates the skin treatment system of FIG. 1 with a portion of the outer housing of the main body portion eliminated to reveal at least a portion of the internal components of the system.

FIG. 8 illustrates a perspective view of the treatment system (e.g., handpiece or handheld device) 10 of FIG. 1 with one portion of the housing removed to expose at least some of the interior components of the system. In the illustrated embodiment, one of the two clamshell pieces that make up the main body portion or housing of the system has been hidden or eliminated. As shown, the system 10 can include a cylindrical member or portion 150 along the receiving area 60. In some embodiments, the cylindrical member 150 is sized, shaped and otherwise configured to receive a similarly shaped pod or other container (not shown in FIG. 8). As noted above, the system 10 can include a piercing member 62 within the interior of the receiving area (e.g., at or along the bottom of the cylindrical member 150) to access the interior of the pod or other container that is properly secured therein.

With continued reference to FIG. 8, the interior of the main body portion can include a circuit board and/or other electronics 110 that are configured to house the various components (e.g., electronic components) of the system, including without limitation, indicator lights and/or other outputs 40, controllers 30, 32, 34, 36 (e.g., ON/OFF button, pressure modification buttons, etc.), processor and/or the like. The interior of the system 10 can also include one or more batteries or other power sources 120 and one or more pumps (e.g., liquid pumps) 130, as desired or required.

As noted herein, batteries 120 included in the system 10 can be rechargeable to permit a user to recharge the battery or batteries between procedures. For instance, in some embodiments, such batteries 120 can be recharged by positioning the main body portion in a docking station 90 (see, e.g., FIG. 1) that is electrically coupled to AC power or another electrical power source. In alternative configurations, the battery (ies), battery pack(s) and/or other power source are configured to be removably positioned within a portion or area of the system. Thus, such batteries can be removed for replacement, disposal, recharging (e.g., in a separate charger or charging device), inspection and/or the like.

In some arrangements, the pump (e.g., liquid pump) 130 included in the system 10 is in fluid communication with the waste conduit system 144, 146 of the system. As shown, the waste conduit system can include at least one conduit or line 144 that extends from or near the tip receiving area 50 to the pump 130 and at least one conduit or line 146 that extends from the pump 130 to or near the waste container or canister 200.

According to some configurations, the pump 130 comprises a liquid pump that contacts (e.g., directly or indirectly) spent liquid and/or other waste materials being transferred from the tip to the waste canister 200. This is contrasted with alternative designs that utilize an air pump to create vacuum within a waste conduit system, but do not actually contact the waste stream being removed. However, for any of the system embodiments disclosed herein, an air pump can be used, either in lieu of or in addition to a liquid pump.

In some embodiments, the pump 130 comprises a diaphragm pump. However, in other embodiments, a different type of pump can be used, as desired or required. For instance, the pump 130 can include, a peristaltic pump (disc-based peristaltic diaphragm pump), a piezoelectric pump, a gear pump, a piston pump, a syringe, another type of micro pump and/or the like. In some embodiments, the pump is able to reliably transfer fluids to and/or from the working end (e.g., from a pod or other container to the tip, from the tip to a waste bin or container, etc.) regardless of the position or orientation of the system (e.g., handpiece, handheld device).

In some embodiments, the use of a liquid pump (e.g., a pump that comes in direct contact with the waste stream being removed from the tip of the system) can allow the pump to create a desired pressure and/or suction effect along the tip of the system during use. For example, the use of such pumps (e.g., diaphragm pump) can allow the system to operate using lower pressures and vacuums. Accordingly, the resulting skin treatment procedure can be more gentle, safer and/or pleasant to the user.

However, in other embodiments, non-liquid based pumps are included in the system (e.g., handpiece), either in lieu of or in additional to liquid pumps. In some embodiments, non-liquid pumps comprise air-based pumps (e.g., pumps that are configured that move air, either continuously or intermittently).

According to some embodiments, the pump (e.g., liquid pump) 130 is configured to create a maximum pressure or vacuum within the waste conduits or lines 144, 146, and thus along the tip 300, of 5 pounds per square inch (psi). In some arrangements, the amount of pressure or vacuum that is generated by the pump can be between 0 and 5 psi (e.g., 0 to 5, 0 to 4, 0 to 3, 0 to 2, 0 to 1, 1 to 5, 1 to 4, 2 to 5, 3 to 5 psi, values between the foregoing, etc.). However, in other embodiments, the liquid pump 130 is configured to generate a maximum pressure or vacuum greater than 5 psi (e.g., 5 to 6, 6 to 7, 7 to 8, 8 to 9, 9 to 10 psi, values between the foregoing, values greater than 10 psi, etc.), as desired or required.

In some embodiments, the system 10 is configured to include two or more (e.g., 2, 3, 4, 5, more than 5, etc.) specific pressure or vacuum levels or values at which the pump 130 can operate. However, in other arrangements, the system 10 can be adapted to permit a user to select any specific pressure or vacuum range. For example, in such configurations, the system can include a dial or other modifiable controller that is not limited to specific (e.g., stepwise) levels of pressure or vacuum. Regardless of the exact configuration of the pump and its operational parameters, the system can include one or more controllers 30 to permit a user to easily and predictably make changes to pressure (e.g., positive or negative) during use of the system. In some embodiments, the system 10 can also be configured to permit a user to modify one or more other operational aspects of the pump 130, such as, for instance, flowrate, pulse rate (e.g., if fluid and/or the associated pressure/vacuum is delivered discontinuously), etc.

According to some embodiments, a pump of the system can be configured to deliver or transfer fluid and/or other treatment materials from a container (e.g., pod) to the tip or working end of the system (e.g., along the system-skin surface interface during use). This can be done in lieu of or in addition to using a pump to draw waste fluids away from the working end (e.g., to a waste bin, canister or other container). In some embodiments, at least one pump is used help deliver fluids and/or other materials to the skin from a treatment material source (e.g., pod, other container, etc.) while at least one pump is used help transfer waste from the working end to a waste container or canister.

With further attention to FIG. 8, as noted above, the system 10 can also include one or more identification tag readers 160. As shown, the reader 160 can be positioned at or near the receiving area 60 for the pod or other container (not shown). For example, the reader 160 can be located immediately adjacent the cylindrical member 150 into which the pod or other container is positioned. In some embodiments, the identification tag reader 160 is configured to read and/or write to a RFID or other type of tag. However, the reader 160 can be configured to read and/or write to any other type of identification tag, as desired or required. The use of identification tags and readers could also be incorporated into any other removable portions or components of the system, such as, for example, the tips, the waste container, etc. The use of such identification systems can enhance the performance, efficiency, safety and/or other aspects related to conducting a skin treatment procedure using any of the system embodiments disclosed herein or equivalents thereof. For example, such technologies can ensure that the proper type of treatment tip (at least a portion of which will contact skin during a treatment procedure) is being used, that the proper materials will be delivered to the skin during a procedure, and/or the like.

Figure 10:
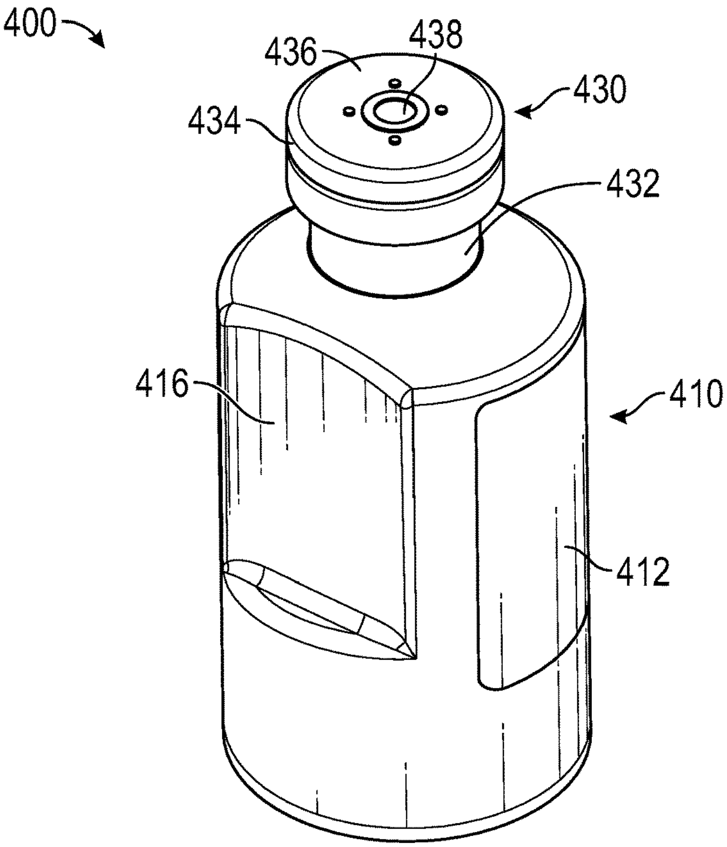
FIG. 10 illustrates a perspective view of a pod or treatment material container configured to be secured to a skin treatment system according to one embodiment.

As illustrated in FIG. 10, a pod or other container 400 can include an identification tag, e.g., RFID tag, along one or more of its surfaces or portions. In some embodiments, the pod 400 includes a flattened portion 416 that is sized, shaped and otherwise arranged to receive an automatic identification tag, such as, for example, a RFID tag or chip, a barcode, etc. Such tags can be used to advantageously store information regarding the specific pod or other treatment material container 400 that may be used in the system 10. For example, the tag can include information regarding the contents of the container, expiration date, manufacturing date, size, lot number, skin procedure with which the contents are intended to be used, other limitations or restrictions on use (e.g., counter-indications, adverse effects, other fluids with which the contents should not be combined, etc.).

The RFID or other identification tag can be read or otherwise detected (e.g., automatically, manually, etc.) by one or more readers or detectors 160 of the system. For example, as shown and discussed above, in some embodiments, the reader 160 is positioned at or near the receiving area 60 of the pod to automatically detect the identification tag of the pod once the pod has been secured to the system. Accordingly, the RFID or other type of reader 160 can advantageously detect and identify the RFID tag of the pod or other container.

According to some embodiments, the RFID or other identification tag reader 160 of the system 10 is configured to both read and write data and/or other information to the tag positioned on the pod or other container. Thus, the information included in the identification tag of the pod or other container 400 can be updated (e.g., continuously, periodically, etc. updated) by the system, as desired or required.

In circumstances where the detected identifier (e.g., whether it is from the pod or container and/or another removable/replaceable component, such as, the tip) is inconsistent with the proper, predicted, safe, appropriate and/or approved operation of the system, the system can be configured to discontinue use of the system (e.g., to prevent fluid and/or other treatment materials included within a pod or other container from being directed to the tip).

The use of the RFID or other identification tags on the pods or other containers 400 and/or other components of the system (e.g., tips) can provide one or more other advantages or benefits. The collection of data regarding use of and/or related to the corresponding container (e.g., pod) can be gathered or otherwise collected to generate reports for billing, reordering and/or other purposes. In some embodiments, the number of times that a pod can be removed and reinserted within a manifold or handpiece or handheld assembly can be limited (e.g., 1, 2, 3, 4, etc.), as desired or required. For example, such limits can help prevent or reduce the likelihood of contamination of the fluid, to prevent the incorrect treatment fluid from being used and/or to provide one or more other benefits, goals and/or advantages. In some embodiments, the automatic identification of the pod or other container being secured to the system can allow the system to determine if a rinse, flush and/or other steps or actions are required before the fluid from that container can be used and/or any other action can be taken in connection with use of the system.

According to some embodiments, the use of RFID or other identification tags can facilitate the execution of a particular skin treatment protocol by the system. For instance, the system can include various pods containing fluids necessary to carry out any one of a number of various skin treatment procedures. For example, a treatment sequence can be configured for use in procedures for periodic or normal microdermabrasion treatment, anti-aging, anti-acne, skin lightening, oily skin treatment and/or the like. Each of the sequences, protocols or modes can include the delivery of one, two or more various serums and/or other fluids or materials that are contained in the pods or other containers.

With continued reference to FIG. 8, the cylindrical member 150 can include a unique shape such that the pod or other container 400 can only be positioned within the member 150 in a particular direction or orientation. For example, as noted above, the cylindrical member 150 can include a flattened portion that corresponds to the flattened portion of the pod. This helps ensure that the RFID or other identification tag reader 160 of the system 10 will be immediately adjacent the corresponding RFID or other identification tag 416 of the pod 400 once the pod has been secured to the system.

In other embodiments, however, the pod or other container 400 need not include a flattened portion or any other unique design or feature. For example, the system can be configured to receive vials with generally continuous cylindrical bodies. Such vials or other containers can be standard or non-standard (e.g., with respect to size, diameter, other dimension, overall shape, etc.). In arrangements where identification tags are utilized, tags can be positioned along any portion of a standard or non-standard vial or container, such as, for example, the neck or top portion, along the exterior of the main cylindrical or other main portion, the bottom, etc.

As with other electrical components of the system 10, the RFID or other identification tag reader (e.g., reader/writer) can be operatively coupled to a circuit board and/or other electronics 110 of the system. Further, as discussed above, any internal electrical components of the system 10 can be operatively coupled (e.g., directly or indirectly, wirelessly or via a wired connection, etc.) to one or more internal components of the system (e.g., processors, memory, controllers, etc.) and/or external computing devices or networks (e.g., a smartphone, a tablet, a personal computer, a separate computing network, a cloud network or infrastructure, a separate skin treatment device or system, etc.) to facilitate processing of data collected by the RFID or other identification tag reader.

FIGS. 9A and 9B illustrate one embodiment of a fluid flow diagram for the skin treatment systems disclosed herein. For example, the schematic flow diagram of FIG. 9A shows the waste conduits, pathways or other lines 144, 146 that place the tip 300 in fluid communication with the liquid pump 130 and the waste container or canister 200. Further, the schematic shows the treatment fluid supply conduit or line 142 that places the pod or other container 400 in fluid communication with the tip 300.

According to some embodiments, once the tip 300 is placed against a user's skin surface and the pump 130 is activated, suction is generated along the tip and the skin surface of the subject undergoing a treatment procedure. If the tip is securely placed along the subject's skin surface, the suction force generated along the tip (by activating, e.g., a liquid pump) will help transfer fluids and/or other treatment materials from the pod 400 to the tip 300 (e.g., via the fluid delivery conduit or line 142). Thus, during operation of the system 10, waste (e.g., spent fluid, exfoliated skin tissue, etc.) can transferred from the tip 300 to the waste canister or container 200. As noted herein, the pump 130 can include a liquid pump that comes in contact (e.g., directly, at least partially, etc.) with the waste material being transferred to the waste canister 200. For example, the pump can be configured such that only certain components and/or portion of the pump actually come in direct contact with the waste being transferred to the waste container. In some arrangements, the pump can include one or more removable or replaceable components, features or portions. Such removable or replaceable components can be configured such that they are entirely, largely or at least partially responsible for coming in direct contact with waste and other materials being transferred to the waste container. In some configurations, the use of such a liquid pump (e.g., a diaphragm pump) can permit the system to operate at lower, more gentle pressure/vacuum levels to create a more pleasant and gentle skin treatment experience for the user.

In some embodiments, the pump is configured such that it is activated or initiated (e.g., automatically) once the tip or other distal portion of the system contacts skin tissue. Relatedly, the pump can be deactivated once the tip or other distal portion of the system no longer contacts skin (e.g., is lifted off the skin surface of the subject being treated). Deactivation can occur immediately or following a time delay, as desired or required. In other arrangements, the system is configured to prevent activation of the pump if contact between the system (e.g., the tip, other distal portion, etc.) and skin is not detected. In order to accomplish the foregoing, one or more sensors (e.g., contact sensors, pressure sensors, temperature sensors, etc.) can be positioned at or near the tip or other distal portion of the system.

FIG. 9B illustrates, in cross-sectional view, one embodiment of a skin treatment system 10. The various internal components of the system 10, including the fluid conduits or lines 142, 144, 146, the pump 130, the waste canister or container 200, the tip 300 and the pod or other container 400 can be seen with representation of fluid flow using arrows. At least a portion of the illustrated internal configuration can be incorporated into any of the system embodiments disclosed herein or equivalents thereof.

With continued attention to FIG. 9B, activation of one or more pumps or other fluid transfer devices of the system can generate a vacuum or suction force along the tip or other distal portion 300 of the system. As a result of such vacuum or suction along or near the tip, fluid conduits, pathways or other lines hydraulically coupling the tip or distal end 300 with a fluid pod or container 400 can transfer serums, fluids and/or other materials from the interior of the pods or other containers secured to the system to and/or near the tip or distal end. Spent fluids or other treatment materials, exfoliated skin tissue, materials removed from the skin surface being treated (e.g., oils, sebum, blackheads, etc.) and/or other waste materials can be transferred from the tip or distal end 300 of the system to a waste container 200.

The embodiment illustrated in FIG. 9B and discussed above is only one configuration of the system's hydraulic network, which includes one or more of the following: fluid conduits, pumps, valves, etc. Alternative ways of transferring treatment material to the tip or other working end and/or removing spent fluids and waste materials from the tip or other working end can be incorporated into any of the embodiments of the system disclosed herein or equivalents thereof.

As noted above, FIG. 10 illustrates one embodiment of a pod or other container 400 configured to be used in the skin treatment system 10. The pod 400 can include a main container portion 410 for containing or housing the serum or other treatment fluid or material. The main container portion 410 can include a tag or label 410. Further, as discussed above, the main container portion 410 can include a flattened or other unique area or portion 416 that is sized, shaped and otherwise adapted to receive a RFID or other identification tag. The container can include a RFID and/or any other type of identification tag or feature along any portion or area (e.g., at, near or along the neck 432 and/or cap 434, its main container portion 410, its bottom portion, etc.), as desired or required. Such tags can be permanently secured to the pod or other container. However, in alternative embodiments, the tags are removably secured to the pod or container, as desired or required.

With further reference to FIG. 10, the pod 400 can include an upper portion 430 that extends from or adjacent the main container portion 410. The upper portion 430 can include a neck 432 and a cap 434. In some embodiments, the cap 434 includes a septum, membrane or other penetrable member 438 along its upper surface 436. As noted herein, such a member 438 can be penetrated or otherwise accessed to selectively place the internal contents of the pod or other container 400 in fluid communication with the system (e.g., fluid delivery conduit, the tip, etc.) once the pod 400 is secured to the receiving area of the system.

According to some embodiments, placement of a pod or other container 400 within the designated recess, slot or other opening of the system aligns the septum or other portion of the pod or container configured to be penetrated or otherwise compromised (e.g., to access the internal contents contained within the pod) with a spike or other protruding member of the system. This can place the contents of the pod or container with one or more fluid conduits, pathways and/or other hydraulic features or components of the system to enable the contents to be selectively delivered to the tip or other distal end of the system.

Figure 11A:
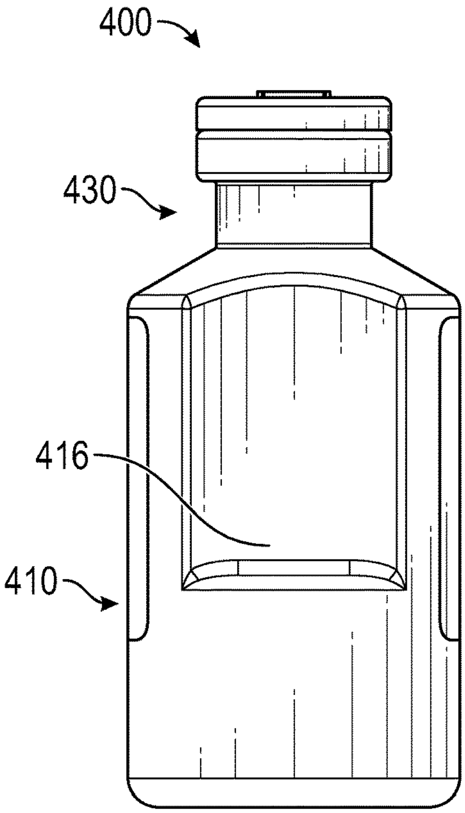
FIGS. 11A and 11B illustrate front and rear views of the pod or container of FIG. 10.
Figure 11B:
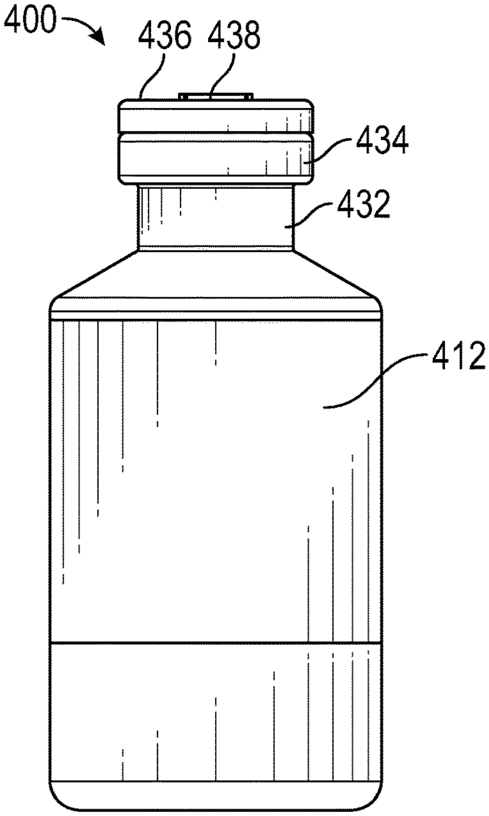
Figure 12A:
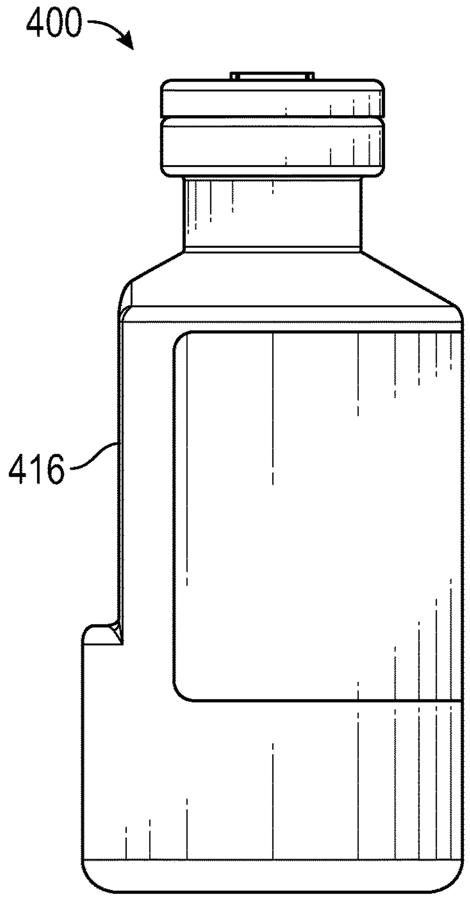
FIGS. 12A and 12B illustrate different side views of the pod or container of FIG. 10.
Figure 12B:
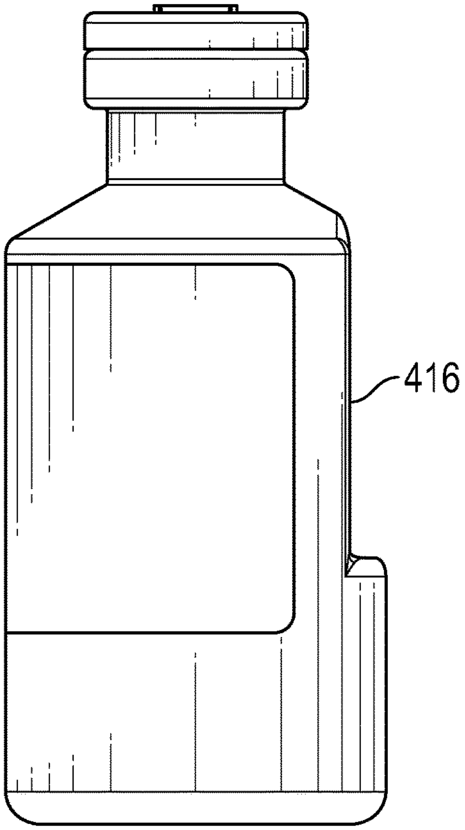
Figure 13A:
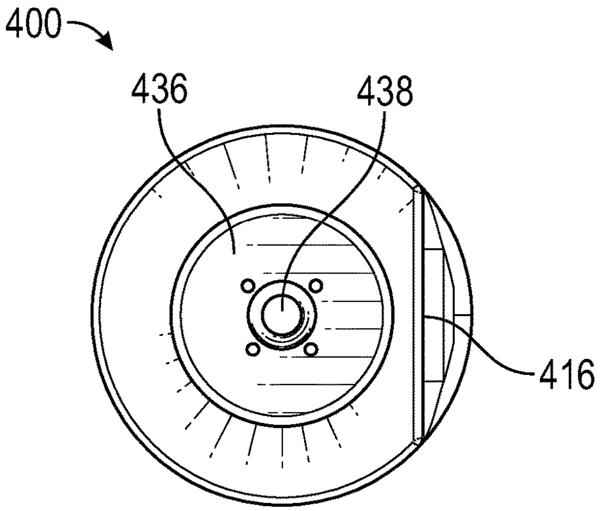
FIGS. 13A and 13B illustrate top and bottom views of the pod or container of FIG. 10.
Figure 13B:
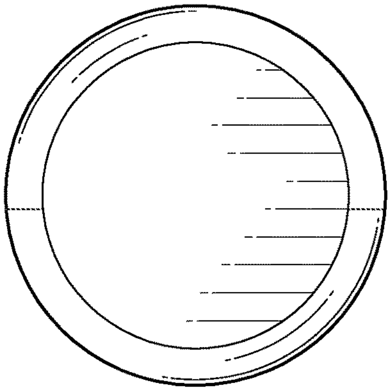

FIGS. 11A and 11B illustrate different side views of the pod 400 of FIG. 10. Further, FIGS. 12A and 12B illustrates front and rear views of the pod 400 of FIG. 10. Finally, FIGS. 13A and 13B illustrate top and bottom views of the pod 400 of FIG. 10.

FIGS. 14 to 17 illustrate a tip 300 configured to be secured to and used with any of the skin treatment embodiments disclosed herein (e.g., the skin treatment system 10 of FIG. 1). As shown, the tip 300 can include a top or distal end 302 and a bottom or proximal end 304. In some embodiments, the tip 300 is configured to secure to the tip receiving area 50 (FIG. 7B) of the main body portion 20. As shown, the tip can include a fluid delivery structure 320 that defines a fluid delivery passage 322 through which serums and/or other treatment materials (e.g., from the pod 400) can flow toward the distal end 302 of the tip. In some embodiments, the fluid delivery structure 320 extends proximally (e.g., past the remaining portions of the tip) in order to facilitate securement of the tip to the main body portion to the tip receiving area 50.

Figure 17:
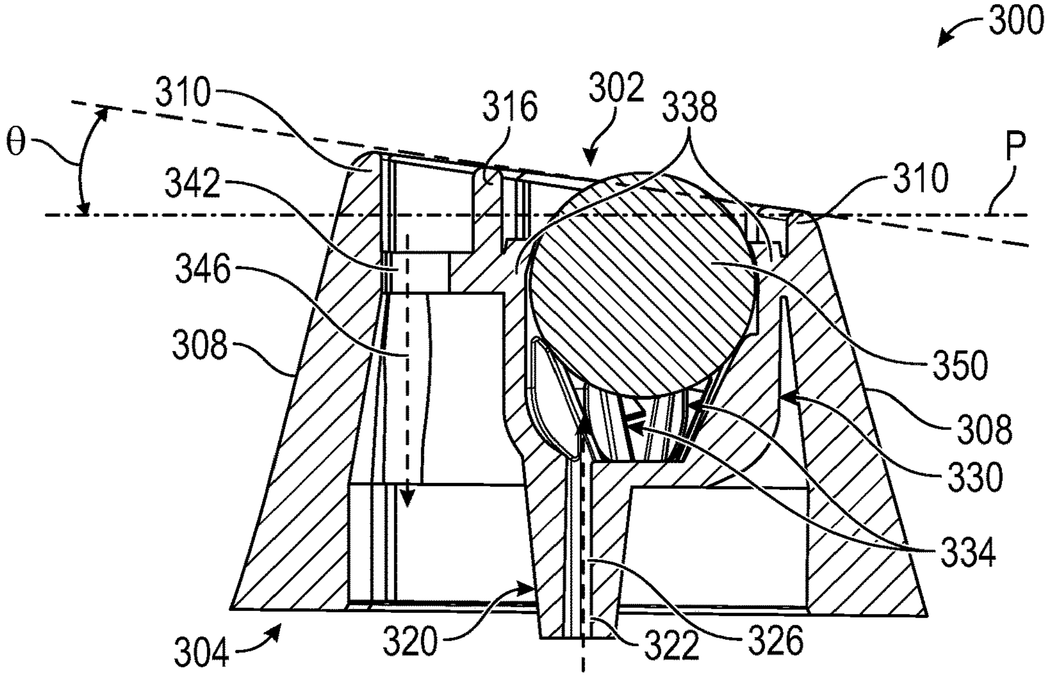
FIG. 17 illustrates a cross-sectional view of the tip of FIG. 14.

As depicted in FIG. 17, the rollerball can be secured within the rollerball housing structure 330 by a series of vanes 334 along its proximal end and one or more retaining lips or members 338 along the distal end. Accordingly, the rollerball 350 can be maintained within the structure 330 and permitted to selectively turn or rotate during use. For example, the rollerball 350 and the adjacent surfaces of the rollerball housing structure 330 can be configured to permit the rollerball to rotate when the rollerball 350 contact skin tissue and is moved relative to said skin tissue. Further, the inclusion of vanes 334 or similar structures along the proximal end of the rollerball 350 can help maintain additional moisture from the treatment fluid along the rollerball during use.

In other embodiments, the tip illustrated in FIGS. 14 to 17 can be modified to exclude a rollerball or similar component or feature. In some embodiments, one or more abrasive structures or portions can be provided in the area where the rollerball is depicted in the illustrated embodiments. Therefore, in such arrangements, the tip can include one or more protrusions, recesses and/or other non-planar features along one or more of its portions or areas.

Figure 14:
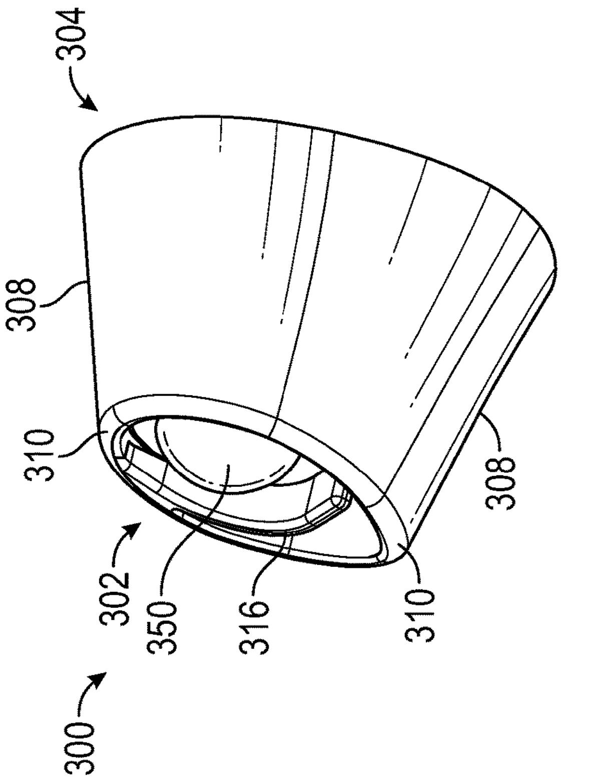
FIG. 14 illustrates a perspective view of a tip configured to be included in a skin treatment system according to one embodiment.

With continued reference to FIGS. 14 and 17, the tip 300 comprises a rollerball 350 that is securely positioned within a rollerball housing structure 330. As illustrated, the rollerball 350 is placed in fluid communication with the fluid delivery passage 322 of the fluid delivery structure 320. Accordingly, serums and/or other treatment liquids or materials passing through passage 322 can be directed to the rollerball 350. In some embodiments, the rollerball is solid and comprises one or more metals and/or alloys. For instance, the rollerball can include a solid stainless steel construction. However, in other embodiments, the rollerball 350 can be at least partially hollow (e.g., not solid). Further, the rollerball 350 can include any other type of metal or alloy and/or other material, as desired or required.

Figure 15B:
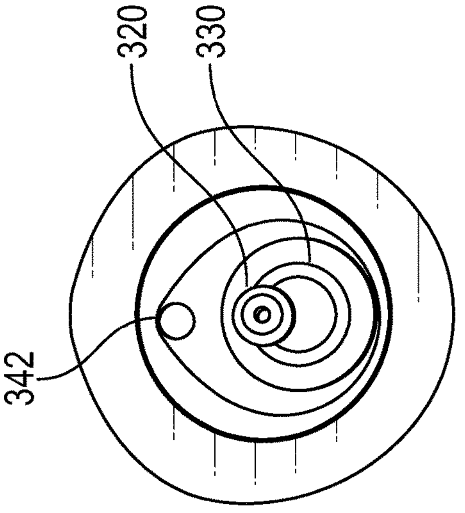
FIGS. 15A and 15B illustrate top and bottom views of the tip of FIG. 14.
Figure 15A:
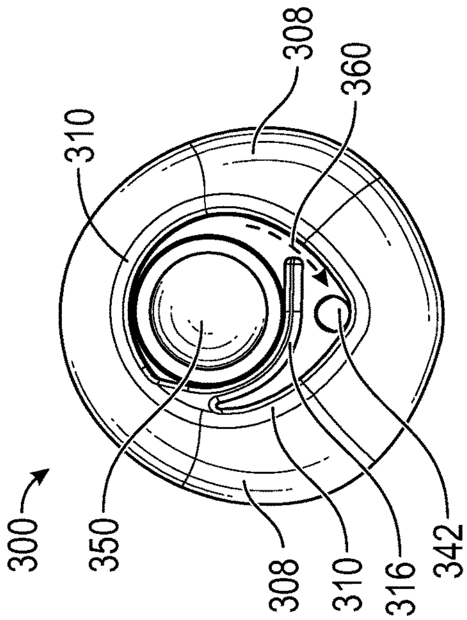
Figure 16A:
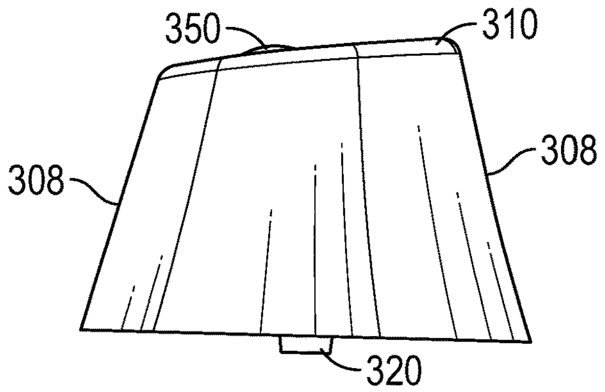
FIGS. 16A and 16B illustrate different side views of the tip of FIG. 14.
Figure 16B:
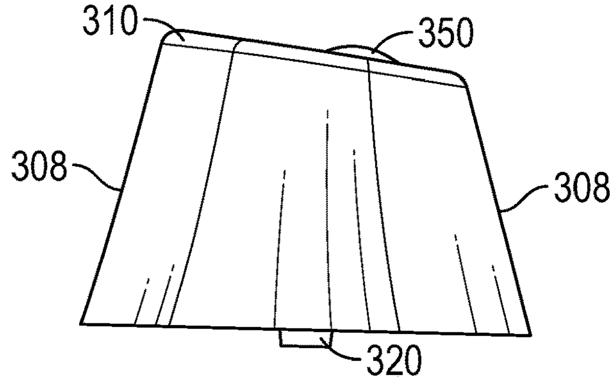

With reference to the top view of the tip 300 illustrated in FIG. 15A, the tip 300 can include a peripheral lip 310 that extends along the outer perimeter along the distal end 302 of the tip. The peripheral lip 310 can be sized, shaped and otherwise configured to contact skin tissue when the skin treatment system 10 is being used. As discussed herein, in some embodiments, the activation of the fluid pump 130 of the system helps create sufficient suction or vacuum along the distal end of the tip so that the peripheral lip 310 can engage tissue during a treatment procedure. This can occur despite the fact that, in some embodiments, such as those illustrated herein, the rollerball extends distally past the distal-most portion of the peripheral lip 310. Thus, in some arrangements, once the liquid pump of the system is activated, the vacuum or suction created along the distal end 302 of the tip 300 can help form at least a partial seal between the peripheral lip 310 of the tip 300 and the skin surface of the subject undergoing a treatment procedure.

As noted above, in some embodiments, the rollerball 350 is sized, shaped and otherwise configured within the tip to extend distally past the distal most portion of the peripheral lip 310. In some arrangements, the rollerball extends 0.8 to 1 mm (0.8 mm to 0.85 mm, 0.85 mm to 0.9 mm, 0.9 mm to 0.95 mm, 0.95 to 1 mm, 0.7 mm to 1 mm, 0.7 mm to 1.2 mm, 0.5 mm to 1.5 mm, less than 0.5 mm, more than 1.5 mm, values between the foregoing, etc.) distally past the peripheral lip 310. According to some embodiments, the rollerball 350 to extend distally past the distal most portion of the peripheral lip by 0.1% to 30% (e.g., 0.1 to 1, 1 to 5, 5 to 10, 10 to 15, 15 to 20, 20 to 25, 25 to 30, 0.1 to 5, 0.1 to 10%, values between the foregoing ranges, greater than 30%, less than 0.1%, etc.) of the diameter or other cross-sectional dimension of the rollerball.

With the application of vacuum along the distal end 302 of the tip (e.g., via activation of the fluid pump of the system), the delivery of treatment fluid from the pod via the fluid delivery conduit, the passage 322 and the rollerball/rollerball housing structure 330 can be enhanced. The arrow 326 in the cross-sectional view of FIG. 17 schematically illustrates the direction of fluid flow through the tip.

With further attention to FIGS. 14, 15A and 17, the tip 300 can additionally include at least one interior baffle or wall 316. Such a baffle or wall 316 can prevent or reduce the likelihood of the short-circuiting of fluid passing through the rollerball 350 to the distal end 302 of the tip 300. In other words, the baffle or wall 316 can create a more tortious pathway of fluid from the rollerball (e.g., fluid passing around the rollerball 350) to the one or more waste ports or outlets 342. FIG. 15A schematically illustrates using arrow 360 fluid passing around the baffle or wall 316 to reduce the amount of flow circuiting of treatment fluid making its way to the distal end 302 of the tip 300. This can advantageously increase the contact time between the treatment fluid and the skin surface being treated during a procedure, thereby enhancing the effectiveness of the procedure.

With continued reference to FIG. 17, waste materials (e.g., spent fluid, skin debris, etc.) can be directed through one or more waste ports or openings 342 and removed from the tip 300 using the vacuum or suction force generated by the pump (e.g., liquid pump). As noted herein, such waste can be transferred from the tip 300 to the waste canister or container 200 using the waste fluid network, 144, 146 and the pump.

According to some embodiments, the tips 300 include one or more plastic materials. In some arrangements, the tips 300 are at least partially translucent or transparent. In some embodiments, the tips 300 are disposable. However, in other arrangements, the tips 300 can be reusable, as desired or required.

As illustrated in FIGS. 14 to 17, the tips can include angled side walls 308. The angles side walls 308 can assist with enhancing the overall look and feel of the treatment system 10 once the tips are secured thereto. For example, as illustrated in FIG. 1, the side slopes of the tip can create a smoother overall look for the assembled system 10.

With continued attention to FIG. 17, the top or distal portion of the tip 300 can be angled relative to a plane P perpendicular to the longitudinal axis of the tip 300 (and the system 10). Such an angle Θ can assist with manipulating the system 10 during use. For example, the angle of the tip 300 can permit the user to tilt the entire system 10 during use provide for a more ergonomic and comfortable execution of a skin treatment procedure. According to some embodiments, the angle Q is between 2 and 10 degrees (e.g., 2 to 3, 3 to 4, 4 to 5, 5 to 6, 6 to 7, 7 to 8, 8 to 9, 9 to 10, 2 to 5, 5 to 8, 8 to 10 degrees, angles between the foregoing ranges and values, etc.). However, in other embodiments, the angle Θ is less than 2 degree or greater than 10 degrees, as desired or required.

In some embodiments, the peripheral lip and/or the internal baffle or wall can be configured to at least partially abrade skin tissue as the system 10 is moved (e.g., translated) relative to a subject's skin tissue. The abrasion can be enhanced with relatively higher suction forces applied by the pump (e.g., liquid pump) to the tip.

According to some embodiments, the various embodiments of a skin treatment system disclosed herein can be self-administered by a user on his or her own (e.g., at home). Such a skin treatment protocol can be a stand-alone procedure to improve the skin health of a subject. However, in other embodiments, the skin treatment embodiments disclosed herein are intended to be used in conjunction with a larger skin treatment regimen that includes periodic professional treatments (e.g., by an aesthetician or other skin treatment professional). For instance, in some arrangements, the skin treatment systems described herein can be used once or twice (or more often) between visits to a skin treatment professional.

According to some embodiments, the skin treatment system 10 disclosed herein can include different treatment steps or phases. For example, in one arrangement, the first step includes a cleansing step. This can be followed up by a secondary hydration step. In some embodiments, additional steps or phases can be used. In some embodiments, different pods can be used for various steps or phases. Therefore, the user may need to remove a first pod or treatment material container 400 from the system and replace with a different one, and vice versa, as desired or required.

Although several embodiments and examples are disclosed herein, the present application extends beyond the specifically disclosed embodiments to other alternative embodiments and/or uses of the inventions and modifications and equivalents thereof. It is also contemplated that various combinations or subcombinations of the specific features and aspects of the embodiments may be made and still fall within the scope of the inventions. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above, but should be determined only by a fair reading of the claims that follow.

While the inventions are susceptible to various modifications, and alternative forms, specific examples thereof have been shown in the drawings and are herein described in detail. It should be understood, however, that the inventions are not to be limited to the particular forms or methods disclosed, but, to the contrary, the inventions are to cover all modifications, equivalents, and alternatives falling within the spirit and scope of the various embodiments described and the appended claims. Any methods disclosed herein need not be performed in the order recited. The methods summarized above and set forth in further detail below describe certain actions taken by a practitioner; however, it should be understood that they can also include the instruction of those actions by another party. The methods summarized above and set forth in further detail below describe certain actions taken by a user (e.g., a professional in some instances); however, it should be understood that they can also include the instruction of those actions by another party. Thus, actions such as "moving a handpiece" or "delivering a fluid" include "instructing moving a handpiece" and "instructing delivering a fluid." The ranges disclosed herein also encompass any and all overlap, sub-ranges, and combinations thereof. Language such as "up to," "at least," "greater than," "less than," "between," and the like includes the number recited. Numbers proceeded by a term such as "about" or "approximately" include the recited numbers. For example, "about 10 mm" includes "10 mm." Terms or phrases preceded by a term such as "substantially" include the recited term or phrase. For example, "substantially parallel" includes "parallel."

What is claimed is:

1. A skin treatment system comprising:

a main body portion, the main body portion comprising a receiving area configured to receive a treatment material container, the main body portion comprising a longitudinal axis;

a waste container configured to be removably secured to the main body portion;

a rechargeable battery;

a base for receiving the main body portion;

a tip configured to be removably secured to the main body portion, the tip comprising a peripheral lip and at least one waste port;

a pump;

at least one fluid delivery conduit placing an interior of a treatment material container secured to the receiving area in fluid communication with the tip; and at least one waste conduit placing the at least one waste port of the tip in fluid communication with the pump, wherein activation of the pump creates a vacuum along the at least one waste conduit and the at least one waste port;

wherein the pump is configured to transfer waste materials from the tip to the waste container via the at least one waste conduit;

wherein the pump is configured to contact waste materials being transferred to the waste container; and wherein the rechargeable battery is configured to be recharged when the main body portion is positioned within the base and the base is operatively coupled to an electric energy source.

2. The system of claim 1, wherein the pump comprises a liquid pump.

3. The system of claim 1, wherein the pump does not comprise an air pump.

4. The system of claim 1, wherein the pump comprises a metering or dosing pump.

5. The system of claim 1, wherein the pump comprises a diaphragm pump.

6. The system of claim 1, wherein the pump comprises one of the following pump types: a peristaltic pump, a piezoelectric pump, a gear pump, a piston pump, a syringe and another type of micro pump.

7. The system of claim 1, wherein the system comprises a handpiece or handheld device configured for personal use by a subject undergoing a skin treatment procedure.

8. The system of claim 1, further comprising at least one controller for regulating at least one operational aspect of the pump.

9. The system of claim 8, wherein the at least one operational aspect of the pump comprises a flowrate and/or pressure of liquid passing through the pump.

10. The system of claim 1, wherein the tip comprises a rollerball, the rollerball positioned within an interior area defined by the peripheral lip and being configured to contact skin when the system is in use.

11. The system of claim 10, wherein the rollerball extends distally past the peripheral lip of the tip.

12. The system of claim 1, wherein the tip comprises at least one interior baffle to reduce a likelihood of short-circuiting fluid flow to the at least one waste port, wherein the at least one interior baffle is positioned within an area defined by the peripheral lip.

13. The system of claim 1, wherein the tip is configured to abrade skin tissue as the system is moved relative to skin tissue of a subject.

14. The system of claim 13, wherein the peripheral lip is configured to at least partially abrade skin tissue as the system is moved relative to skin tissue of a subject.

15. The system of claim 1, wherein the pump is configured to create suction along the tip when the longitudinal axis of the main body portion is maintained at an angle between 0 and 110 degrees relative to vertical.

16. The system of claim 1, further comprising at least one illumination source configured to provide light to the waste container.

17. The system of claim 16, wherein the at least one illumination source comprises at least one light emitting diode (LED).

18. The system of claim 1, wherein a suction created at the tip by the pump is 0 to 5 pounds per square inch (psi).

19. The system of claim 1, wherein a maximum suction created at the tip by the pump is 5 pounds per square inch (psi).

20. The system of claim 1, wherein the receiving area is configured to receive a disposable pod.

* * * * *